United States Patent
Cheng et al.

(10) Patent No.: US 7,074,588 B2
(45) Date of Patent: Jul. 11, 2006

(54) CAROTENOID KETOLASE GENE

(75) Inventors: Qiong Cheng, Wilmington, DE (US); Luan Tao, Havertown, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 68 days.

(21) Appl. No.: 11/152,747

(22) Filed: Jun. 14, 2005

(65) Prior Publication Data

US 2005/0251881 A1  Nov. 10, 2005

Related U.S. Application Data

(62) Division of application No. 10/209,372, filed on Jul. 30, 2002.

(60) Provisional application No. 60/309,653, filed on Aug. 2, 2001.

(51) Int. Cl.
*C12P 23/00* (2006.01)
*C12N 9/10* (2006.01)

(52) U.S. Cl. .......................... 435/67; 435/193
(58) Field of Classification Search .................. None
See application file for complete search history.

(56) References Cited

U.S. PATENT DOCUMENTS 5,750,865 A  5/1998  Bird et al.

FOREIGN PATENT DOCUMENTS

WO  WO 02/18617 A2  3/2002

OTHER PUBLICATIONS

Hannibal et al., Isolation and Characterization of Canthaxanthin Biosynthesis Genes from the Photosynthetic Bacterium Brandyrhizobium sp. Strain ORS278, J. Bacteriol.(2000) 182: 3850-3853.
Fernandez-Gonzalez et al., A New Type of Asymmetrically Acting β-Carotene Ketolase Is Required for the Synthesis of Echinenone in the Cyanobacterium Synechocystis sp. PCC 6803, J.of Biol. Chem.(1997) 272;9728-9733.
Mann et al., Metabolic engineering of astaxanthin production in tobacco flowers, (2000) Nature Biotechnology, 18:888-892.
Ichiyama et al., Carotenoid Pigments of Genus Rhodococcus, Microbiol. Immunol. (1989), 33:503-508.
White O et al., Genome Sequence of the Radioresistant Bacterium Deinococcus radiodurans R1, Science 286 (5444), 1571-1577 (1999).
NCBI, Accession No. NC00091, Synechocystis CrtO(slr0088), Oct. 23, 2001.
NCBI, Accession No. AE001872, Deinococcus gene (DR0093), Nov. 22, 1999.
P.C. Lee et al., Metabolic Engineering Towards Biotechnological Production Of Carotenoids In Microorganisms, Appl. Microbiol. Biotechnol., 2000, pp. 1-11, vol. 60.

*Primary Examiner*—Charles L. Patterson, Jr.

(57) ABSTRACT

A ketolase gene has been isolated from *Rhodococcus erythropolis* AN12 strain encoding a carotenoid modification enzyme of the carotenoid biosynthetic pathway. The gene and gene product are the first isolated from a *Rhodococcus* strain. Six conserved amino acid motifs have been identified as the characteristic of this type of ketolase enzymes. The gene and gene product of the present invention may be used in a variety of ways for the production of keto-carotenoid compounds in a variety of organisms.

14 Claims, 6 Drawing Sheets

Figure 1:
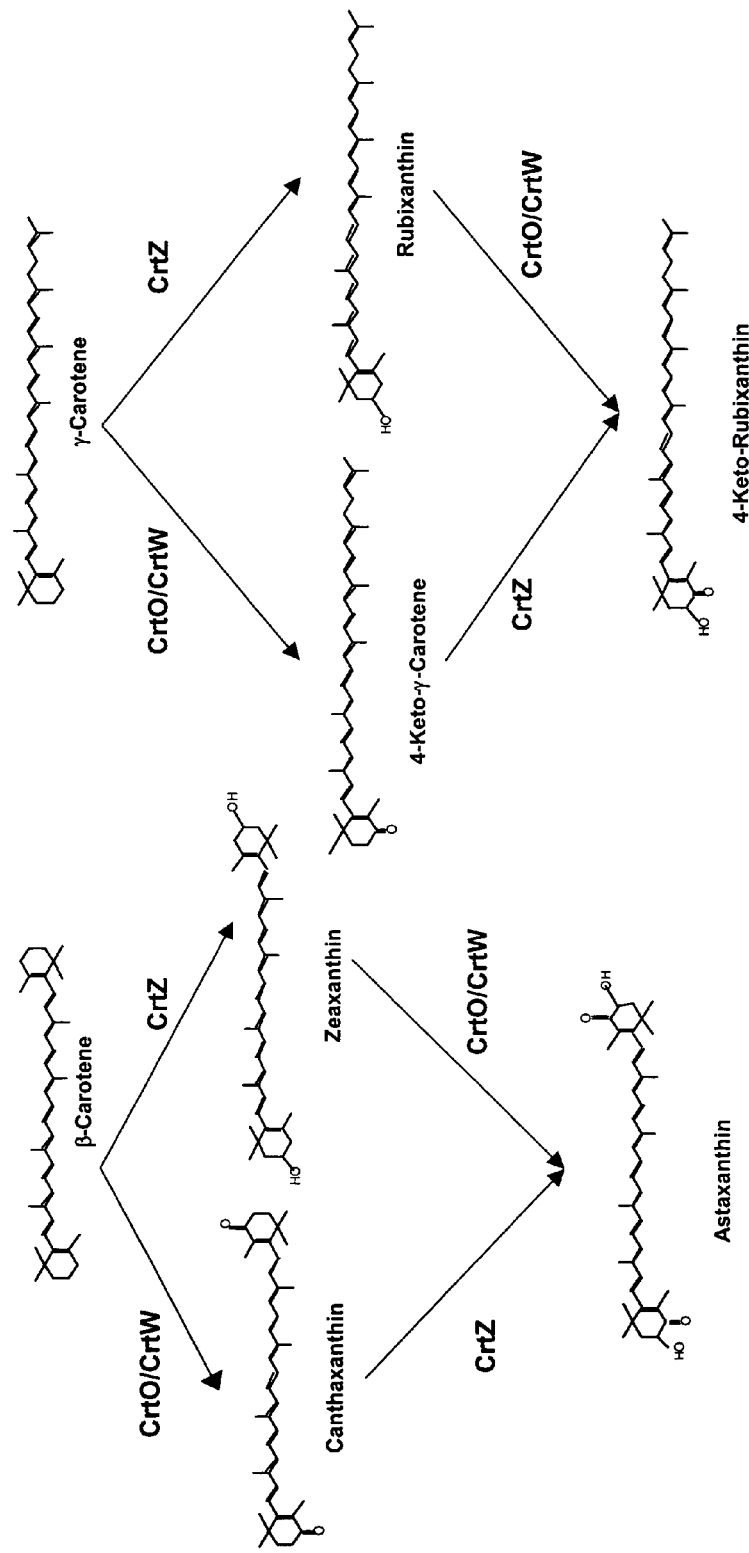

FIGURE 5
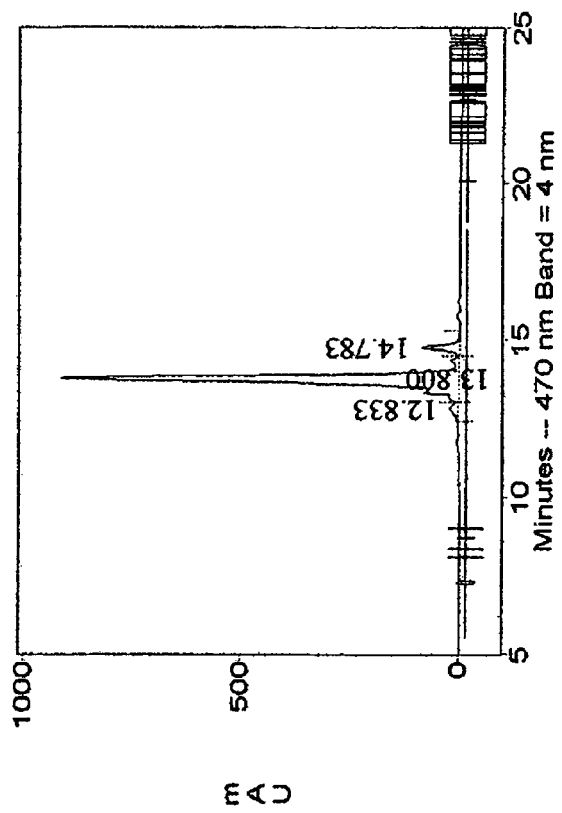
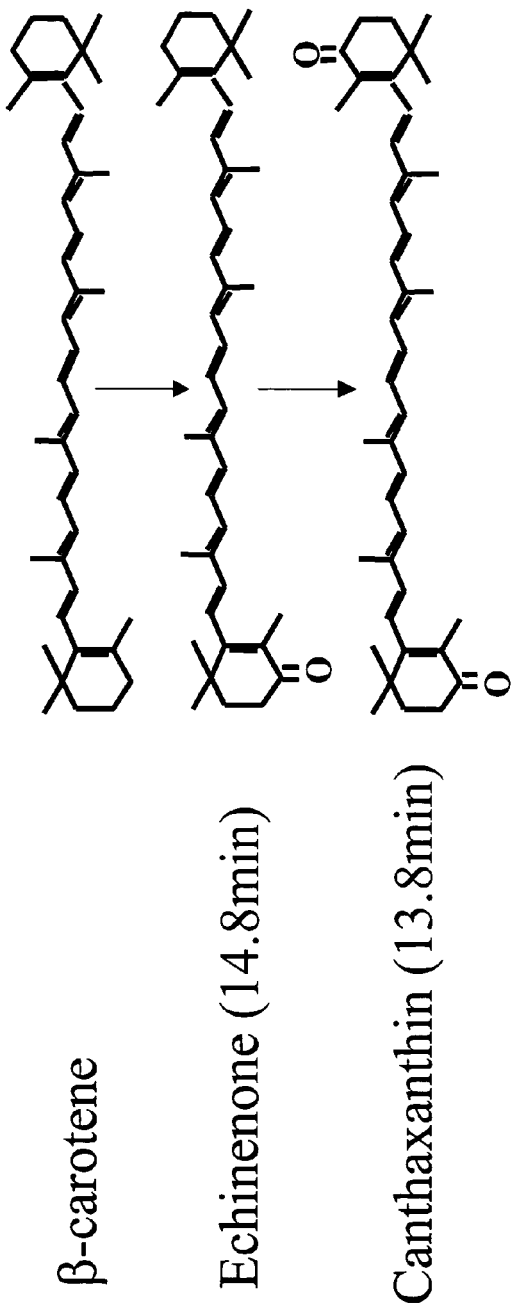
β-carotene
Echinenone (14.8min)
Canthaxanthin (13.8min)

SEQUENCE LISTING

<160> NUMBER OF SEQ ID NOS: 47

<210> SEQ ID NO 1
<211> LENGTH: 1599
<212> TYPE: DNA
<213> ORGANISM: Rhodococcus erythropolis AN12

<400> SEQUENCE: 1

```
gtgagcgcat ttctcgacgc cgtcgtcgtc ggttccggac acaacgcgct cgtttcggcc      60
gcgtatctcg cacgtgaggg ttggtcggtc gaggttctcg agaaggacac ggttctcggc     120
ggtgccgtct cgaccgtcga gcgatttccc ggatacaagg tggaccgggg gtcgtctgcg     180
cacctcatga tccgacacag tggcatcatc gaggaactcg gactcggcgc gcacggcctt     240
cgctacatcg actgtgaccc gtgggcgttc gctccgcccg ccctggcac cgacgggccg      300 ggcatcgtgt ttcatcgcga cctcgatgca acctgccagt ccatcgaacg agcttgcggg     360
acaaaggacg ccgacgcgta ccggcggttc gtcgcggtct ggtcggagcg cagccgacac     420
gtgatgaagg cattttccac accgcccacc ggatcgaacc tgatcggtgc gttcggagga     480
ctggccacag cgcgcggcaa cagcgaactg tcgcggcagt cctcgcgcc gggcgacgca     540 ctgctggacg agtatttcga cagtgaggca ctcaaggcag cgttggcgtg gttcggcgcc     600
cagtccgggc ctccgatgtc ggaaccggga accgctccga tggtcggctt cgcggccctc     660
atgcacgtcc tgccgcccgg gcgagcagtc ggagggagcg gcgcactgag tgctgcgttg     720
gcatcccgga tggctgtcga cggcgccacc gtcgcgctcg gtgacggcgt gacgtcgatc     780
cgccggaact cgaatcactg gaccgtcaca accgagagcg gtcgagaagt tcacgctcgc     840
aaggtaatcg cgggttgcca catcctcacg acactcgatc tcctgggcaa cggaggcttc     900
gaccgaacca cgctcgatca ctggcggcgg aagatcaggg tcggcccggg catcggcgct     960
gtattgcgac tggcgacatc tgcgctcccg tcctaccgcg gcgacgccac gacacgggaa    1020
agtacctcgg gattgcaatt actcgtttcc gatcgcgccc acttgcgcac tgcacacggc    1080
gcagcactgg caggggaact gcctcctcgc cctgcggttc tcggaatgag tttcagcgga    1140
atcgatccca cgatcgcccc ggccgggcgg catcaggtga cactgtggtc gcagtggcag    1200
ccgtatcgtc tcagcggaca tcgcgattgg gcgtcggtcg ccgaggccga ggccgaccgg    1260
```

```
atcgtcggcg agatggaggc ttttgcaccc ggattcaccg attccgtcct cgaccgcttc    1320
attcaaactc cccgcgacat cgagtcggaa ttggggatga tcggcggaaa tgtcatgcac    1380
gtcgagatgt cactcgatca gatgatgttg tggcgaccgc ttcccgaact gtccggccat    1440
cgcgttccgg gagcagacgg gttgtatctg accggagcct cgacgcatcc cggtggtggt    1500
gtgtccggag ccagtggtcg cagtgccgct cgaatcgcac tgtccgacag ccgccggggt    1560
aaagcgagtc agtggatgcg tcgttcgagc aggtcgtga                          1599
```

<210> SEQ ID NO 2
<211> LENGTH: 532
<212> TYPE: PRT
<213> ORGANISM: Rhodococcus erythropolis AN12

<400> SEQUENCE: 2

```
Val Ser Ala Phe Leu Asp Ala Val Val Gly Ser Gly His Asn Ala
1               5                   10                  15

Leu Val Ser Ala Ala Tyr Leu Ala Arg Glu Gly Trp Ser Val Glu Val
                20                  25                  30

Leu Glu Lys Asp Thr Val Leu Gly Gly Ala Val Ser Thr Val Glu Arg
            35                  40                  45

Phe Pro Gly Tyr Lys Val Asp Arg Gly Ser Ser Ala His Leu Met Ile
        50                  55                  60

Arg His Ser Gly Ile Ile Glu Glu Leu Gly Leu Gly Ala His Gly Leu
65                  70                  75                  80

Arg Tyr Ile Asp Cys Asp Pro Trp Ala Phe Ala Pro Pro Ala Pro Gly
                85                  90                  95

Thr Asp Gly Pro Gly Ile Val Phe His Arg Asp Leu Asp Ala Thr Cys
            100                 105                 110

Gln Ser Ile Glu Arg Ala Cys Gly Thr Lys Asp Ala Asp Ala Tyr Arg
        115                 120                 125

Arg Phe Val Ala Val Trp Ser Glu Arg Ser Arg His Val Met Lys Ala
    130                 135                 140

Phe Ser Thr Pro Pro Thr Gly Ser Asn Leu Ile Gly Ala Phe Gly Gly
145                 150                 155                 160

Leu Ala Thr Ala Arg Gly Asn Ser Glu Leu Ser Arg Gln Phe Leu Ala
                165                 170                 175

Pro Gly Asp Ala Leu Leu Asp Glu Tyr Phe Asp Ser Glu Ala Leu Lys
            180                 185                 190

Ala Ala Leu Ala Trp Phe Gly Ala Gln Ser Gly Pro Pro Met Ser Glu
        195                 200                 205

Pro Gly Thr Ala Pro Met Val Gly Phe Ala Ala Leu Met His Val Leu
    210                 215                 220

Pro Pro Gly Arg Ala Val Gly Gly Ser Gly Ala Leu Ser Ala Ala Leu
225                 230                 235                 240

Ala Ser Arg Met Ala Val Asp Gly Ala Thr Val Ala Leu Gly Asp Gly
                245                 250                 255

Val Thr Ser Ile Arg Arg Asn Ser Asn His Trp Thr Val Thr Thr Glu
            260                 265                 270

Ser Gly Arg Glu Val His Ala Arg Lys Val Ile Ala Gly Cys His Ile
        275                 280                 285

Leu Thr Thr Leu Asp Leu Leu Gly Asn Gly Gly Phe Asp Arg Thr Thr
    290                 295                 300

Leu Asp His Trp Arg Arg Lys Ile Arg Val Gly Pro Gly Ile Gly Ala
```

```
             305                 310                 315                 320
Val Leu Arg Leu Ala Thr Ser Ala Leu Pro Ser Tyr Arg Gly Asp Ala
                325                 330                 335

Thr Thr Arg Glu Ser Thr Ser Gly Leu Gln Leu Leu Val Ser Asp Arg
                340                 345                 350

Ala His Leu Arg Thr Ala His Gly Ala Ala Leu Ala Gly Glu Leu Pro
                355                 360                 365

Pro Arg Pro Ala Val Leu Gly Met Ser Phe Ser Gly Ile Asp Pro Thr
370                 375                 380

Ile Ala Pro Ala Gly Arg His Gln Val Thr Leu Trp Ser Gln Trp Gln
385                 390                 395                 400

Pro Tyr Arg Leu Ser Gly His Arg Asp Trp Ala Ser Val Ala Glu Ala
                405                 410                 415

Glu Ala Asp Arg Ile Val Gly Glu Met Glu Ala Phe Ala Pro Gly Phe
                420                 425                 430

Thr Asp Ser Val Leu Asp Arg Phe Ile Gln Thr Pro Arg Asp Ile Glu
                435                 440                 445

Ser Glu Leu Gly Met Ile Gly Gly Asn Val Met His Val Glu Met Ser
450                 455                 460

Leu Asp Gln Met Met Leu Trp Arg Pro Leu Pro Glu Leu Ser Gly His
465                 470                 475                 480

Arg Val Pro Gly Ala Asp Gly Leu Tyr Leu Thr Gly Ala Ser Thr His
                485                 490                 495

Pro Gly Gly Gly Val Ser Gly Ala Ser Gly Arg Ser Ala Ala Arg Ile
                500                 505                 510

Ala Leu Ser Asp Ser Arg Arg Gly Lys Ala Ser Gln Trp Met Arg Arg
                515                 520                 525

Ser Ser Arg Ser
530

<210> SEQ ID NO 3
<211> LENGTH: 1536
<212> TYPE: DNA
<213> ORGANISM: Deinococcus radiodurans R1

<400> SEQUENCE: 3
atgccggatt acgacctgat cgtcatgggc gcgggccaca cgcgctggt gactgctgcc     60 tacgccgccc gggcgggcct gaaagtcggc gtgttcgagc ggcggcacct cgtcggcggg    120
gcggtcagca ccgaggaggt cgtgcccggt taccgcttcg actacggcgg cagcgcccac    180
atcctgattc ggatgacgcc catcgtgcgc gaactcgaac tcacgcggca cgggctgcat    240
tacctcgaag tggaccctat gtttcacgct tccgacggtg aaacgccctg gttcattcac    300
cgcgacgccg gcggaccat ccgcgaactg gacgaaaagt ttcccgggca gggcgacgcc    360 tacggcgcgct ttctcgacga ttggacaccc ttcgcgcgcg ccgtggccga cctgttcaac    420
tcggcgccgg ggccgctcga cctgggcaaa atggtgatgc cagcggcca gggcaaggac    480 tggaacgagc agctcccgcg catcctgcgg ccctacggcg acgtggcgcg cgagtacttc    540
agcgaggagc gcgtgcgggc tcccctgacc tggatggcgg cccagagcgg cccccaccc    600 tcggacccgc tgagcgcgcc ctttttgctg tggcacccgc tctaccacga aggcggcgtg    660
gcgcggccca aggcggcag cggcggcctg accaaagccc tgcgccgggc caccgaggcc    720
gaaggcggcg aggtcttcac cgacgcgccg gtcaaggaaa ttctggtcaa ggacggcaag    780
gcgcagggca tccggctgga aagcggcgag acgtacaccg cccgcgccgt cgtgtcgggc    840
```

-continued

```
gtccacatcc tgaccactgc gaatgccctg cccgccgaat atgtccctag cgccgccagg     900
aatgtgcgcg tgggcaacgg cttcggcatg attttgcgcc tcgccctcag tgaaaaagtc     960
aaataccgtc accacaccga gcccgactca cgcatcggcc tgggattgct gatcaaaaac    1020
gagcggcaaa tcatgcaggg ctacggcgaa tacctcgccg ggcagccaac caccgacccg    1080
cccctcgtcg ccatgagctt cagcgcggtg acgactcgc tcgccccacc gaacggcgac    1140
gtgttgtggc tgtgggcgca gtactacccc ttcgagctcg ccaccgggag ctgggaaacg    1200
cgcaccgccg aagcgcggga gaacatcctg cgggcctttg agcactacgc gccgggcacc    1260
cgcgacacga ttgtgggcga actcgtgcag acgccgcagt ggctggaaac caacctcggc    1320
ctgcaccggg gcaacgtgat gcacctggaa atgtccttcg accagatgtt ctccttccgc    1380
ccctggctga aagcgagcca gtaccgctgg ccgggcgtgc aggggctgta cctcaccggc    1440
gccagcaccc accccggcgg aggcatcatg ggcgcctcgg gacgcaacgc ggcgcgggtc    1500
atcgtgaagg acctgacgcg gaggcgctgg aaatga                              1536
```

<210> SEQ ID NO 4
<211> LENGTH: 511
<212> TYPE: PRT
<213> ORGANISM: Deinococcus radiodurans R1

<400> SEQUENCE: 4

```
Met Pro Asp Tyr Asp Leu Ile Val Met Gly Ala Gly His Asn Ala Leu
 1               5                  10                  15

Val Thr Ala Ala Tyr Ala Ala Arg Ala Gly Leu Lys Val Gly Val Phe
            20                  25                  30

Glu Arg Arg His Leu Val Gly Gly Ala Val Ser Thr Glu Glu Val Val
        35                  40                  45

Pro Gly Tyr Arg Phe Asp Tyr Gly Gly Ser Ala His Ile Leu Ile Arg
    50                  55                  60

Met Thr Pro Ile Val Arg Glu Leu Glu Leu Thr Arg His Gly Leu His
65                  70                  75                  80

Tyr Leu Glu Val Asp Pro Met Phe His Ala Ser Asp Gly Glu Thr Pro
                85                  90                  95

Trp Phe Ile His Arg Asp Ala Gly Arg Thr Ile Arg Glu Leu Asp Glu
            100                 105                 110

Lys Phe Pro Gly Gln Gly Asp Ala Tyr Gly Arg Phe Leu Asp Asp Trp
        115                 120                 125

Thr Pro Phe Ala Arg Ala Val Ala Asp Leu Phe Asn Ser Ala Pro Gly
    130                 135                 140

Pro Leu Asp Leu Gly Lys Met Val Met Arg Ser Gly Gln Gly Lys Asp
145                 150                 155                 160

Trp Asn Glu Gln Leu Pro Arg Ile Leu Arg Pro Tyr Gly Asp Val Ala
                165                 170                 175

Arg Glu Tyr Phe Ser Glu Glu Arg Val Arg Ala Pro Leu Thr Trp Met
            180                 185                 190

Ala Ala Gln Ser Gly Pro Pro Ser Asp Pro Leu Ser Ala Pro Phe
        195                 200                 205

Leu Leu Trp His Pro Leu Tyr His Glu Gly Val Ala Arg Pro Lys
    210                 215                 220

Gly Gly Ser Gly Gly Leu Thr Lys Ala Leu Arg Arg Ala Thr Glu Ala
225                 230                 235                 240

Glu Gly Gly Glu Val Phe Thr Asp Ala Pro Val Lys Glu Ile Leu Val
```

```
                    245                 250                 255
Lys Asp Gly Lys Ala Gln Gly Ile Arg Leu Glu Ser Gly Glu Thr Tyr
                260                 265                 270

Thr Ala Arg Ala Val Val Ser Gly Val His Ile Leu Thr Thr Ala Asn
            275                 280                 285

Ala Leu Pro Ala Glu Tyr Val Pro Ser Ala Ala Arg Asn Val Arg Val
        290                 295                 300

Gly Asn Gly Phe Gly Met Ile Leu Arg Leu Ala Leu Ser Glu Lys Val
305                 310                 315                 320

Lys Tyr Arg His His Thr Glu Pro Asp Ser Arg Ile Gly Leu Gly Leu
                325                 330                 335

Leu Ile Lys Asn Glu Arg Gln Ile Met Gln Gly Tyr Gly Glu Tyr Leu
            340                 345                 350

Ala Gly Gln Pro Thr Thr Asp Pro Pro Leu Val Ala Met Ser Phe Ser
        355                 360                 365

Ala Val Asp Asp Ser Leu Ala Pro Pro Asn Gly Asp Val Leu Trp Leu
    370                 375                 380

Trp Ala Gln Tyr Tyr Pro Phe Glu Leu Ala Thr Gly Ser Trp Glu Thr
385                 390                 395                 400

Arg Thr Ala Glu Ala Arg Glu Asn Ile Leu Arg Ala Phe Glu His Tyr
                405                 410                 415

Ala Pro Gly Thr Arg Asp Thr Ile Val Gly Glu Leu Val Gln Thr Pro
            420                 425                 430

Gln Trp Leu Glu Thr Asn Leu Gly Leu His Arg Gly Asn Val Met His
        435                 440                 445

Leu Glu Met Ser Phe Asp Gln Met Phe Ser Phe Arg Pro Trp Leu Lys
    450                 455                 460

Ala Ser Gln Tyr Arg Trp Pro Gly Val Gln Gly Leu Tyr Leu Thr Gly
465                 470                 475                 480

Ala Ser Thr His Pro Gly Gly Gly Ile Met Gly Ala Ser Gly Arg Asn
                485                 490                 495

Ala Ala Arg Val Ile Val Lys Asp Leu Thr Arg Arg Trp Lys
            500                 505                 510

<210> SEQ ID NO 5
<211> LENGTH: 1629
<212> TYPE: DNA
<213> ORGANISM: Synechocystis sp. PCC6803

<400> SEQUENCE: 5
atgatcacca ccgatgttgt cattattggg gcggggcaca atggcttagt ctgtgcagcc    60
tatttgctcc aacggggctt ggggtgacg ttactagaaa agcgggaagt accagggggg    120
gcggccacca cagaagctct catgccggag ctatcccccc agtttcgctt taaccgctgt    180
gccattgacc acgaatttat ctttctgggg ccggtgttgc aggagctaaa tttagcccag    240
tatggtttgg aatatttatt ttgtgacccc agtgtttttt gtccggggct ggatggccaa    300
gcttttatga gctaccgttc cctagaaaaa acctgtgccc acattgccac ctatagcccc    360
cgagatgcgg aaaaatatcg gcaatttgtc aattattgga cggatttgct caacgctgtc    420
cagcctgctt ttaatgctcc gccccaggct ttactagatt tagccctgaa ctatggttgg    480
gaaaacttaa atccgtgctg gcgatcgcc gggtcgaaaa ccaaggcgtt ggattttatc    540
cgcactatga tcggctcccc ggaagatgtg ctcaatgaat ggttcgacag cgaacgggtt    600
aaagctcctt tagctagact atgttcggaa attggcgctc ccccatccca aagggtagt    660
```

```
agctccggca tgatgatggt ggccatgcgg catttggagg gaattgccag accaaaagga      720
ggcactggag ccctcacaga agccttggtg aagttagtgc aagcccaagg gggaaaaatc      780
ctcactgacc aaaccgtcaa acgggtattg gtggaaaaca accaggcgat cggggtggag      840
gtagctaacg agaacagta ccgggccaaa aaaggcgtga tttctaacat cgatgcccgc       900
cgtttatttt tgcaattggt ggaaccgggg ccctagcca aggtgaatca aaacctaggg       960
gaacgactgg aacggcgcac tgtgaacaat aacgaagcca ttttaaaaat cgattgtgcc     1020
ctctccggtt tacccactt cactgccatg gccgggccgg aggatctaac gggaactatt      1080
ttgattgccg actcggtacg ccatgtcgag aagcccacg ccctcattgc cttggggcaa      1140
attcccgatg ctaatccgtc tttatatttg gatattccca ctgtattgga ccccaccatg     1200
gccccccctg ggcagcacac cctctggatc gaatttttg ccccctaccg catcgccggg      1260
ttggaaggga cagggttaat gggcacaggt tggaccgatg agttaaagga aaaagtggcg     1320
gatcgggtga ttgataaatt aacggactat gcccctaacc taaaatctct gatcattggt     1380
cgccgagtgg aaagtcccgc cgaactggcc caacggctgg gaagttacaa cggcaatgtc     1440
tatcatctgg atatgagttt ggaccaaatg atgttcctcc ggcctctacc ggaaattgcc     1500
aactaccaaa cccccatcaa aaatctttac ttaacagggg cgggtaccca tcccggtggc     1560
tccatatcag gtatgcccgg tagaaattgc gctcgggtct ttttaaaaca acaacgtcgt     1620
ttttggtaa                                                             1629

<210> SEQ ID NO 6
<211> LENGTH: 542
<212> TYPE: PRT
<213> ORGANISM: Synechocystis sp. PCC6803

<400> SEQUENCE: 6

Met Ile Thr Thr Asp Val Ile Ile Gly Ala Gly His Asn Gly Leu
 1               5                  10                  15

Val Cys Ala Ala Tyr Leu Leu Gln Arg Gly Leu Gly Val Thr Leu Leu
            20                  25                  30

Glu Lys Arg Glu Val Pro Gly Gly Ala Ala Thr Thr Glu Ala Leu Met
        35                  40                  45

Pro Glu Leu Ser Pro Gln Phe Arg Phe Asn Arg Cys Ala Ile Asp His
    50                  55                  60

Glu Phe Ile Phe Leu Gly Pro Val Leu Gln Glu Leu Asn Leu Ala Gln
65                  70                  75                  80

Tyr Gly Leu Glu Tyr Leu Phe Cys Asp Pro Ser Val Phe Cys Pro Gly
                85                  90                  95

Leu Asp Gly Gln Ala Phe Met Ser Tyr Arg Ser Leu Glu Lys Thr Cys
           100                 105                 110

Ala His Ile Ala Thr Tyr Ser Pro Arg Asp Ala Glu Lys Tyr Arg Gln
       115                 120                 125

Phe Val Asn Tyr Trp Thr Asp Leu Leu Asn Ala Val Gln Pro Ala Phe
   130                 135                 140

Asn Ala Pro Pro Gln Ala Leu Leu Asp Leu Ala Leu Asn Tyr Gly Trp
145                 150                 155                 160

Glu Asn Leu Lys Ser Val Leu Ala Ile Ala Gly Ser Lys Thr Lys Ala
                165                 170                 175

Leu Asp Phe Ile Arg Thr Met Ile Gly Ser Pro Glu Asp Val Leu Asn
           180                 185                 190
```

```
Glu Trp Phe Asp Ser Glu Arg Val Lys Ala Pro Leu Ala Arg Leu Cys
            195                 200                 205

Ser Glu Ile Gly Ala Pro Ser Gln Lys Gly Ser Ser Ser Gly Met
    210                 215                 220

Met Met Val Ala Met Arg His Leu Glu Gly Ile Ala Arg Pro Lys Gly
225                 230                 235                 240

Gly Thr Gly Ala Leu Thr Glu Ala Leu Val Lys Leu Val Gln Ala Gln
                245                 250                 255

Gly Gly Lys Ile Leu Thr Asp Gln Thr Val Lys Arg Val Leu Val Glu
            260                 265                 270

Asn Asn Gln Ala Ile Gly Val Glu Val Ala Asn Gly Glu Gln Tyr Arg
        275                 280                 285

Ala Lys Lys Gly Val Ile Ser Asn Ile Asp Ala Arg Arg Leu Phe Leu
    290                 295                 300

Gln Leu Val Glu Pro Gly Ala Leu Ala Lys Val Asn Gln Asn Leu Gly
305                 310                 315                 320

Glu Arg Leu Glu Arg Arg Thr Val Asn Asn Asn Glu Ala Ile Leu Lys
                325                 330                 335

Ile Asp Cys Ala Leu Ser Gly Leu Pro His Phe Thr Ala Met Ala Gly
            340                 345                 350

Pro Glu Asp Leu Thr Gly Thr Ile Leu Ile Ala Asp Ser Val Arg His
        355                 360                 365

Val Glu Glu Ala His Ala Leu Ile Ala Leu Gly Gln Ile Pro Asp Ala
    370                 375                 380

Asn Pro Ser Leu Tyr Leu Asp Ile Pro Thr Val Leu Asp Pro Thr Met
385                 390                 395                 400

Ala Pro Pro Gly Gln His Thr Leu Trp Ile Glu Phe Phe Ala Pro Tyr
                405                 410                 415

Arg Ile Ala Gly Leu Glu Gly Thr Gly Leu Met Gly Thr Gly Trp Thr
            420                 425                 430

Asp Glu Leu Lys Glu Lys Val Ala Asp Arg Val Ile Asp Lys Leu Thr
        435                 440                 445

Asp Tyr Ala Pro Asn Leu Lys Ser Leu Ile Ile Gly Arg Arg Val Glu
    450                 455                 460

Ser Pro Ala Glu Leu Ala Gln Arg Leu Gly Ser Tyr Asn Gly Asn Val
465                 470                 475                 480

Tyr His Leu Asp Met Ser Leu Asp Gln Met Met Phe Leu Arg Pro Leu
                485                 490                 495

Pro Glu Ile Ala Asn Tyr Gln Thr Pro Ile Lys Asn Leu Tyr Leu Thr
            500                 505                 510

Gly Ala Gly Thr His Pro Gly Gly Ser Ile Ser Gly Met Pro Gly Arg
        515                 520                 525

Asn Cys Ala Arg Val Phe Leu Lys Gln Gln Arg Arg Phe Trp
530                 535                 540
```

<210> SEQ ID NO 7
<211> LENGTH: 8
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Position 1 can be Asp or Glu
<220> FEATURE:
<221> NAME/KEY: MISC_FEATURE

```
<222> LOCATION: (4)..(4)
<223> OTHER INFORMATION: Position 4 can be Phe or Leu
<220> FEATURE:
<221> NAME/KEY: MISC_FEATURE
<222> LOCATION: (8)..(8)
<223> OTHER INFORMATION: Position 8 can be Met or Phe

<400> SEQUENCE: 7

Xaa Met Ser Xaa Asp Gln Met Xaa
1               5

<210> SEQ ID NO 8
<211> LENGTH: 9
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (6)..(6)
<223> OTHER INFORMATION: Position 6 can be Ser of Gly

<400> SEQUENCE: 8

Tyr Leu Thr Gly Ala Xaa Thr His Pro
1               5

<210> SEQ ID NO 9
<211> LENGTH: 10
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Position 1 can be His or Tyr
<220> FEATURE:
<221> NAME/KEY: MISC_FEATURE
<222> LOCATION: (4)..(4)
<223> OTHER INFORMATION: Position 4 can be Arg, His or Glu
<220> FEATURE:
<221> NAME/KEY: MISC_FEATURE
<222> LOCATION: (6)..(6)
<223> OTHER INFORMATION: Position 6 can be Ile or Leu
<220> FEATURE:
<221> NAME/KEY: MISC_FEATURE
<222> LOCATION: (7)..(7)
<223> OTHER INFORMATION: Position 7 can be Asp, Glu or Phe
<220> FEATURE:
<221> NAME/KEY: MISC_FEATURE
<222> LOCATION: (8)..(8)
<223> OTHER INFORMATION: Position 8 can be Cys or Val

<400> SEQUENCE: 9

Xaa Gly Leu Xaa Tyr Xaa Xaa Xaa Asp Pro
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (3)..(3)
<223> OTHER INFORMATION: Position 3 can be Ala or Gly
<220> FEATURE:
<221> NAME/KEY: MISC_FEATURE
<222> LOCATION: (6)..(6)
<223> OTHER INFORMATION: Position 6 can be Ser, Thr or Cys

<400> SEQUENCE: 10
```

```
His Asn Xaa Leu Val Xaa Ala Ala Tyr
1               5
```

<210> SEQ ID NO 11
<211> LENGTH: 10
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: Position 2 can be Tyr or Trp
<220> FEATURE:
<221> NAME/KEY: MISC_FEATURE
<222> LOCATION: (4)..(4)
<223> OTHER INFORMATION: Position 4 can be Asp or Ser
<220> FEATURE:
<221> NAME/KEY: MISC_FEATURE
<222> LOCATION: (5)..(5)
<223> OTHER INFORMATION: Position 5 can be Ser or Glu
<220> FEATURE:
<221> NAME/KEY: MISC_FEATURE
<222> LOCATION: (7)..(7)
<223> OTHER INFORMATION: Position 7 can be Arg or Ala
<220> FEATURE:
<221> NAME/KEY: MISC_FEATURE
<222> LOCATION: (8)..(8)
<223> OTHER INFORMATION: Position 8 can be Val or Leu
<220> FEATURE:
<221> NAME/KEY: MISC_FEATURE
<222> LOCATION: (9)..(9)
<223> OTHER INFORMATION: Position 9 can be Lys or Arg

<400> SEQUENCE: 11

```
Glu Xaa Phe Xaa Xaa Glu Xaa Xaa Xaa Ala
1               5                   10
```

<210> SEQ ID NO 12
<211> LENGTH: 8
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: Position 2 can be either Arg or Gly
<220> FEATURE:
<221> NAME/KEY: MISC_FEATURE
<222> LOCATION: (3)..(3)
<223> OTHER INFORMATION: Position 3 can be either Arg or Gln
<220> FEATURE:
<221> NAME/KEY: MISC_FEATURE
<222> LOCATION: (5)..(5)
<223> OTHER INFORMATION: Position 5 can be either Val or Leu
<220> FEATURE:
<221> NAME/KEY: MISC_FEATURE
<222> LOCATION: (6)..(6)
<223> OTHER INFORMATION: Position 6 can be either Ala, Asp or Asn
<220> FEATURE:
<221> NAME/KEY: MISC_FEATURE
<222> LOCATION: (7)..(7)
<223> OTHER INFORMATION: Position 7 can be either Asp, Val or Tyr

<400> SEQUENCE: 12

```
Tyr Xaa Xaa Phe Xaa Xaa Xaa Trp
1               5
```

<210> SEQ ID NO 13
<211> LENGTH: 27
<212> TYPE: DNA
<213> ORGANISM: Artificial Sequence

```
<220> FEATURE:
<223> OTHER INFORMATION: Primer

<400> SEQUENCE: 13
ccatggtctg cgcacctcat gatccga                                   27

<210> SEQ ID NO 14
<211> LENGTH: 27
<212> TYPE: DNA
<213> ORGANISM: Artificial sequence
<220> FEATURE:
<223> OTHER INFORMATION: Primer

<400> SEQUENCE: 14
ccatggaatg aagcggtcga ggacgga                                   27

<210> SEQ ID NO 15
<211> LENGTH: 18
<212> TYPE: DNA
<213> ORGANISM: Artificial sequence
<220> FEATURE:
<223> OTHER INFORMATION: Primer

<400> SEQUENCE: 15
agcggcatca gcaccttg                                             18

<210> SEQ ID NO 16
<211> LENGTH: 21
<212> TYPE: DNA
<213> ORGANISM: Artificial sequence
<220> FEATURE:
<223> OTHER INFORMATION: Primer

<400> SEQUENCE: 16
gccaatatgg acaacttctt c                                         21

<210> SEQ ID NO 17
<211> LENGTH: 20
<212> TYPE: DNA
<213> ORGANISM: Artificial sequence
<220> FEATURE:
<223> OTHER INFORMATION: Primer

<400> SEQUENCE: 17
acctgaggtg ttcgacgagg                                           20

<210> SEQ ID NO 18
<211> LENGTH: 28
<212> TYPE: DNA
<213> ORGANISM: Artificial sequence
<220> FEATURE:
<223> OTHER INFORMATION: Primer

<400> SEQUENCE: 18
gttgcacagt ggtcatcgtg ccagccgt                                  28

<210> SEQ ID NO 19
<211> LENGTH: 21
<212> TYPE: DNA
<213> ORGANISM: Artificial sequence
<220> FEATURE:
<223> OTHER INFORMATION: Primer

<400> SEQUENCE: 19
atgagcgcat ttctcgacgc c                                         21
```

```
<210> SEQ ID NO 20
<211> LENGTH: 20
<212> TYPE: DNA
<213> ORGANISM: Artificial sequence
<220> FEATURE:
<223> OTHER INFORMATION: Primer

<400> SEQUENCE: 20
tcacgacctg ctcgaacgac                                               20

<210> SEQ ID NO 21
<211> LENGTH: 22
<212> TYPE: DNA
<213> ORGANISM: Artificial sequence
<220> FEATURE:
<223> OTHER INFORMATION: Primer

<400> SEQUENCE: 21
atgccggatt acgacctgat cg                                            22

<210> SEQ ID NO 22
<211> LENGTH: 22
<212> TYPE: DNA
<213> ORGANISM: Artificial sequence
<220> FEATURE:
<223> OTHER INFORMATION: Primer

<400> SEQUENCE: 22
tcatttccag cgcctccgcg tc                                            22

<210> SEQ ID NO 23
<211> LENGTH: 19
<212> TYPE: DNA
<213> ORGANISM: Artificial sequence
<220> FEATURE:
<223> OTHER INFORMATION: Primer

<400> SEQUENCE: 23
gagtttgatc ctggctcag                                                19

<210> SEQ ID NO 24
<211> LENGTH: 16
<212> TYPE: DNA
<213> ORGANISM: Artificial sequence
<220> FEATURE:
<223> OTHER INFORMATION: Primer

<400> SEQUENCE: 24
taccttgtta cgactt                                                   16

<210> SEQ ID NO 25
<211> LENGTH: 17
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (11)..(11)
<223> OTHER INFORMATION: Y = C or T
<220> FEATURE:
<221> NAME/KEY: misc_feature
<222> LOCATION: (12)..(12)
<223> OTHER INFORMATION: M = A or C

<400> SEQUENCE: 25
gtgccagcag ymgcggt                                                  17
```

-continued

<210> SEQ ID NO 26
<211> LENGTH: 8
<212> TYPE: PRT
<213> ORGANISM: Rhodococcus erythropolis AN12

<400> SEQUENCE: 26

Glu Met Ser Leu Asp Gln Met Met
1               5

<210> SEQ ID NO 27
<211> LENGTH: 9
<212> TYPE: PRT
<213> ORGANISM: Rhodococcus erythropolis AN12

<400> SEQUENCE: 27

Tyr Leu Thr Gly Ala Ser Thr His Pro
1               5

<210> SEQ ID NO 28
<211> LENGTH: 10
<212> TYPE: PRT
<213> ORGANISM: Rhodococcus erythropolis AN12

<400> SEQUENCE: 28

His Gly Leu Arg Tyr Ile Asp Cys Asp Pro
1               5               10

<210> SEQ ID NO 29
<211> LENGTH: 9
<212> TYPE: PRT
<213> ORGANISM: Rhodococcus erythropolis AN12

<400> SEQUENCE: 29

His Asn Ala Leu Val Ser Ala Ala Tyr
1               5

<210> SEQ ID NO 30
<211> LENGTH: 10
<212> TYPE: PRT
<213> ORGANISM: Rhodococcus erythropolis AN12

<400> SEQUENCE: 30

Glu Tyr Phe Asp Ser Glu Ala Leu Lys Ala
1               5               10

<210> SEQ ID NO 31
<211> LENGTH: 8
<212> TYPE: PRT
<213> ORGANISM: Rhodococcus erythropolis AN12

<400> SEQUENCE: 31

Tyr Arg Arg Phe Val Ala Val Trp
1               5

<210> SEQ ID NO 32
<211> LENGTH: 8
<212> TYPE: PRT
<213> ORGANISM: Deinococcus radiodurans

<400> SEQUENCE: 32

Glu Met Ser Phe Asp Gln Met Phe
1               5

```
<210> SEQ ID NO 33
<211> LENGTH: 9
<212> TYPE: PRT
<213> ORGANISM: Deinococcus radiodurans

<400> SEQUENCE: 33

Tyr Leu Thr Gly Ala Ser Thr His Pro
1               5

<210> SEQ ID NO 34
<211> LENGTH: 10
<212> TYPE: PRT
<213> ORGANISM: Deinococcus radiodurans

<400> SEQUENCE: 34

His Gly Leu His Tyr Leu Glu Val Asp Pro
1               5                   10

<210> SEQ ID NO 35
<211> LENGTH: 9
<212> TYPE: PRT
<213> ORGANISM: Deinococcus radiodurans

<400> SEQUENCE: 35

His Asn Ala Leu Val Thr Ala Ala Tyr
1               5

<210> SEQ ID NO 36
<211> LENGTH: 10
<212> TYPE: PRT
<213> ORGANISM: Deinococcus radiodurans

<400> SEQUENCE: 36

Glu Tyr Phe Ser Glu Glu Arg Val Arg Ala
1               5                   10

<210> SEQ ID NO 37
<211> LENGTH: 8
<212> TYPE: PRT
<213> ORGANISM: Deinococcus radiodurans

<400> SEQUENCE: 37

Tyr Gly Arg Phe Leu Asp Asp Trp
1               5

<210> SEQ ID NO 38
<211> LENGTH: 8
<212> TYPE: PRT
<213> ORGANISM: Synechocystis sp. strain PCC6803

<400> SEQUENCE: 38

Asp Met Ser Leu Asp Gln Met Met
1               5

<210> SEQ ID NO 39
<211> LENGTH: 9
<212> TYPE: PRT
<213> ORGANISM: Synechocystis sp. strain PCC6803

<400> SEQUENCE: 39

Tyr Leu Thr Gly Ala Gly Thr His Pro
1               5

<210> SEQ ID NO 40
<211> LENGTH: 10
```

```
<212> TYPE: PRT
<213> ORGANISM: Synechocystis sp. strain PCC6803

<400> SEQUENCE: 40

Tyr Gly Leu Glu Tyr Leu Phe Cys Asp Pro
1               5                   10

<210> SEQ ID NO 41
<211> LENGTH: 9
<212> TYPE: PRT
<213> ORGANISM: Synechocystis sp. strain PCC6803

<400> SEQUENCE: 41

His Asn Gly Leu Val Cys Ala Ala Tyr
1               5

<210> SEQ ID NO 42
<211> LENGTH: 10
<212> TYPE: PRT
<213> ORGANISM: Synechocystis sp. strain PCC6803

<400> SEQUENCE: 42

Glu Trp Phe Asp Ser Glu Arg Val Lys Ala
1               5                   10

<210> SEQ ID NO 43
<211> LENGTH: 8
<212> TYPE: PRT
<213> ORGANISM: Synechocystis sp. strain PCC6803

<400> SEQUENCE: 43

Tyr Arg Gln Phe Val Asn Tyr Trp
1               5

<210> SEQ ID NO 44
<211> LENGTH: 25
<212> TYPE: DNA
<213> ORGANISM: Artificial Sequence
<220> FEATURE:
<223> OTHER INFORMATION: Primer

<400> SEQUENCE: 44
atgacggtct gcgcaaaaaa acacg                                        25

<210> SEQ ID NO 45
<211> LENGTH: 28
<212> TYPE: DNA
<213> ORGANISM: Artificial Sequence
<220> FEATURE:
<223> OTHER INFORMATION: Primer

<400> SEQUENCE: 45
gagaaattat gttgtggatt tggaatgc                                     28

<210> SEQ ID NO 46
<211> LENGTH: 21
<212> TYPE: DNA
<213> ORGANISM: Artificial Sequence
<220> FEATURE:
<223> OTHER INFORMATION: Primer

<400> SEQUENCE: 46
atgagcgcat ttctcgacgc c                                            21

<210> SEQ ID NO 47
```

```
<211> LENGTH: 20
<212> TYPE: DNA
<213> ORGANISM: Artificial Sequence
<220> FEATURE:
<223> OTHER INFORMATION: Primer

<400> SEQUENCE: 47
tcacgacctg ctcgaacgac                                              20
```

CAROTENOID KETOLASE GENE

This application is a division of Ser. No. 10/209,372 filed Jul. 30, 2002 which claims benefit of U.S. Provisional Application No. 60/309,653 filed Aug. 2, 2001.

FIELD OF THE INVENTION

This invention is in the field of microbiology. More specifically, this invention pertains to nucleic acid fragments encoding enzymes useful for microbial production of cyclic ketocarotenoid compounds.

BACKGROUND OF THE INVENTION

Carotenoids are pigments that are ubiquitous throughout nature and synthesized by all photosynthetic organisms, and in some heterotrophic growing bacteria and fungi. Carotenoids provide color for flowers, vegetables, insects, fish and birds. Colors of carotenoid range from yellow to red with variations of brown and purple. As precursors of vitamin A, carotenoids are fundamental components in our diet and they play additional important role in human health. Industrial uses of carotenoids include pharmaceuticals, food supplements, animal feed additives and colorants in cosmetics to mention a few.

Because animals are unable to synthesize carotenoid de novo, they must obtain them by dietary means. Thus, manipulation of carotenoid production and composition in plants or bacteria can provide new or improved source for carotenoids.

Carotenoids come in many different forms and chemical structures. Most naturally occurring carotenoids are hydrophobic tetraterpenoids containing a $C_{40}$ methyl-branched hydrocarbon backbone derived from successive condensation of eithght $C_5$ isoprene units (IPP). In addition, rare carotenoids with longer or shorter backbones occur in some species of nonphotosynthetic bacteria. The term "carotenoid" actually include both carotenes and xanthophylls. A "carotene" refers to a hydrocarbon carotenoid. Carotene derivatives that contain one or more oxygen atoms, in the form of hydroxy-, methoxy-, oxo-, epoxy-, carboxy-, or aldehydic functional groups, or within glycosides, glycoside esters, or sulfates, are collectively known as "xanthophylls". Carotenoids are furthermore described as being acyclic, monocyclic, or bicyclic depending on whether the ends of the hydrocarbon backbones have been cyclized to yield aliphatic or cyclic ring structures (G. Armstrong, (1999) In Comprehensive Natural Products Chemistry, Elsevier Press, volume 2, pp 321–352).

Carotenoid biosynthesis starts with the isoprenoid pathway and the generation of a C5 isoprene unit, isopentenyl pyrophosphate (IPP). IPP is condensed with its isomer dimethylallyl pyrophophate (DMAPP) to form the C10, geranyl pyrophosphate (GPP), and elongated to the C15, farnesyl pyrophosphate (FPP). FPP synthesis is common to both carotenogenic and non-carotenogenic bacteria. Enzymes in subsequent carotenoid pathways generate carotenoid pigments from the FPP precursor and can be divided into two categories: carotene backbone synthesis enzymes and subsequent modification enzymes. The backbone synthesis enzymes include geranyl geranyl pyrophosphate synthase, phytoene synthase, phytoene dehydrogenase and lycopene cyclase, etc. The modification enzymes include ketolases, hydroxylases, dehydratases, glycosylases, etc.

Carotenoid ketolases are a class of enzymes that introduce keto groups to the ionone ring of the cyclic carotenoids such as β-carotene to produce ketocarotenoids. Ketocarotenoids include astaxanthin, canthaxanthin, adonixanthin, adonirubin, echinenone, 3-hydroxyechinenone, 3'-hydroxyechinenone, 4-keto-gamma-carotene, 4-keto-rubixanthin, 4-keto-torulene, 3-hydroxy-4-keto-torulene, deoxyflexixanthin, myxobactone. Astaxanthin was reported to boost immune functions in humans, and, reduce carcinogenesis in animals. Unlike genes in the upstream isoprenoid pathway that are common in all organisms, the downstream carotenoid modifying enzymes are rare. Two classes of ketolase, CrtW and CrtO, have been reported. The CrtW is a symmetrically acting enzyme that adds keto-groups to both rings of β-carotene (Hannibal et al., *J. Bacteriol.* (2000) 182: 3850–3853). Fernández-González et al. (*J. of Biol. Chem.* (1997) 272;9728–9733) has discovered another ketolase enzyme, CrtO, from *Synechocystis* sp. PCC6803 that adds a keto-group asymmetrically to only one β-carotene rings. The crtO gene from *Haematococcus pluvialis* has been transferred to tobacco pant to express astaxanthin in the plant (Mann et al., (2000) *Nature Biotechnology*, 18:888–892).

Although the genes involved in carotenoid biosynthesis pathways are known in some organisms, genes involved in carotenoid biosynthesis in *Rhodococcus* bacteria are not described in the existing literature. However, there are many pigmented *Rhodococcus* bacteria suggesting that the ability to produce carotenoid pigments is widespread in these bacteria. Carotenoids of *Rhodococcus* have been structurally characterized in *Rhodococcus* as described by Ichiyama et al., (*Microbiol. Immunol.* (1989), 33:503–508).

The problem to be solved therefore is to isolate sequences involved in carotenoid biosynthesis in *Rhodococcus* for their eventual use in carotenoid production. Applicants have solved the stated problem by isolating a gene, crtO, from a *Rhodococcus erythropolis* AN12 strain containing an open reading frame (ORF) encoding a ketolase enzyme that contains 6 conserved diagnostic amino acid motifs that are the characteristic of this type of ketolase enzymes.

SUMMARY OF THE INVENTION

The present invention provides a keto carotenoid gene encoding an enzyme which adds keto groups to the ionone ring of the cyclic carotenoids. Accordingly the invention provides an isolated nucleic acid molecule encoding a carotenoid ketolase enzyme, selected from the group consisting of:
  (a) an isolated nucleic acid molecule encoding an amino acid sequence containing all six conserved motifs as set forth in SEQ ID NOs:7, 8, 9, 10, 11 and 12;
  (b) an isolated nucleic acid molecule encoding the amino acid sequence SEQ ID NO:2;
  (c) an isolated nucleic acid molecule that hybridizes with (a) or (b) under the following hybridization conditions: 0.1×SSC, 0.1% SDS, 65° C. and washed with 2×SSC, 0.1% SDS followed by 0.1×SSC, 0.1% SDS; or
  an isolated nucleic acid molecule that is complementary to (a), or (b), wherein the isolated nucleic acid molecule is not SEQ ID NO:5 or SEQ ID NO:3.

The invention additionally provides polypeptides encoded by the present gene as well as genetic chimera of the present gene, and recombinant hosts comprising the gene. Genes encoding carotenoid ketolases having at least 70% identity to the instant polypeptide are also within the scope of the invention.

In another embodiment the invention provides a method of obtaining a nucleic acid molecule encoding a carotenoid ketolase enzyme comprising:

(a) probing a genomic library with the nucleic acid molecule of the present invention;
(b) identifying a DNA clone that hybridizes with the nucleic acid molecule of the present invention under the following hybridization conditions: 0.1×SSC, 0.1% SDS, 65° C. and washed with 2×SSC, 0.1% SDS followed by 0.1×SSC, 0.1% SDS; and
(c) sequencing the genomic fragment that comprises the clone identified in step (b), wherein the sequenced genomic fragment encodes a carotenoid ketolase enzyme.

Similarly the invention provides a method of obtaining a nucleic acid molecule encoding a carotenoid ketolase enzyme comprising:
(a) synthesizing at least one oligonucleotide primer corresponding to a portion of the sequence selected from the group consisting of SEQ ID NO:1 and SEQ ID NO:3; and
(b) amplifying an insert present in a cloning vector using the oligonucleotide primer of step (a);

wherein the amplified insert encodes a carotenoid ketolase enzyme.

In another embodiment the invention provides a method for the production of cyclic ketocarotenoid compounds comprising:
(a) providing a host cell which produces monocyclic or bicyclic carotenoids;
(b) transforming the host cell of (a) with a gene encoding a carotenoid ketolase enzyme, the enzyme having an amino acid sequence selected from the group consisting of SEQ ID NO:2 and SEQ ID NO:4; and
(c) growing the transformed host cell of (b) under conditions whereby a cyclic ketocarotenoid is produced.

Similarly the invention provides a method of regulating cyclic ketocarotenoid biosynthesis in an organism comprising,
(a) introducing into a host cell a carotenoid ketolase gene selected from the group consisting of SEQ ID NO:1 and SEQ ID NO:3, said gene under the control of suitable regulatory sequences; and
(b) growing the host cell of (a) under conditions whereby the carotenoid ketolase gene is expressed and cyclic ketocarotenoid biosynthesis is regulated.

In an alternate embodiment the invention provides a mutated gene encoding a carotenoid ketolase enzyme having an altered biological activity produced by a method comprising the steps of:
(i) digesting a mixture of nucleotide sequences with restriction endonucleases wherein said mixture comprises:
a) a native carotenoid ketolase gene;
b) a first population of nucleotide fragments which will hybridize to said native carotenoid ketolase gene;
c) a second population of nucleotide fragments which will not hybridize to said native carotenoid ketoalse gene;

wherein a mixture of restriction fragments are produced;
(ii) denaturing said mixture of restriction fragments;
(iii) incubating the denatured said mixture of restriction fragments of step (ii) with a polymerase;
(iv) repeating steps (ii) and (iii) wherein a mutated carotenoid ketoalse gene is produced encoding a protein having an altered biological activity.

BRIEF DESCRIPTION OF THE DRAWINGS AND SEQUENCE DESCRIPTIONS

FIG. 1 describes common carotenoid products produced by ketolase in conjunction with hydroxylase enzyme.

Figure 2:
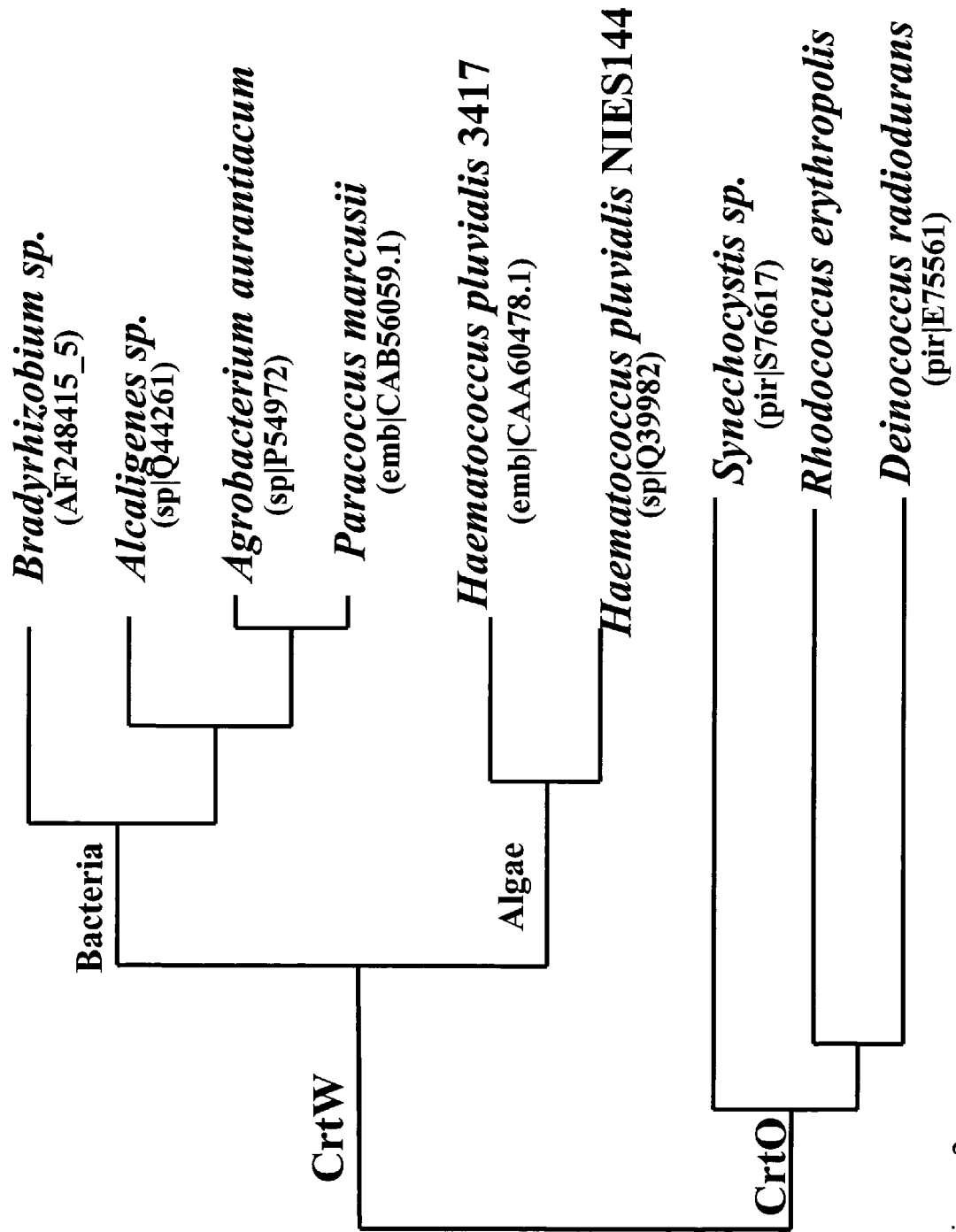

FIG. 2 describes the Phylogenetic relationship of the carotenoid ketolases.

Figure 3:
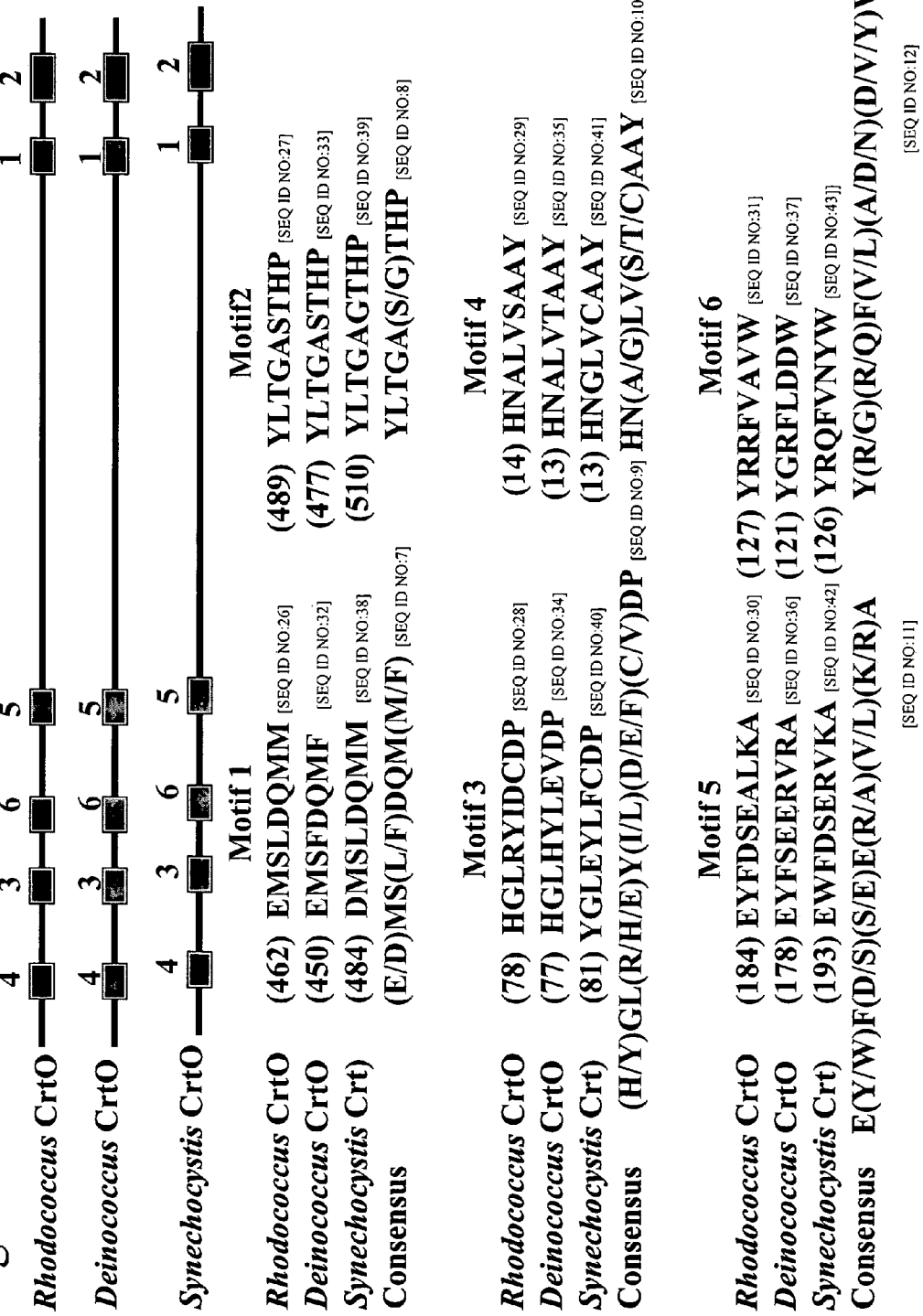

FIG. 3 describes conserved motifs identified in the CrtO-type of ketolases.

Figure 4:
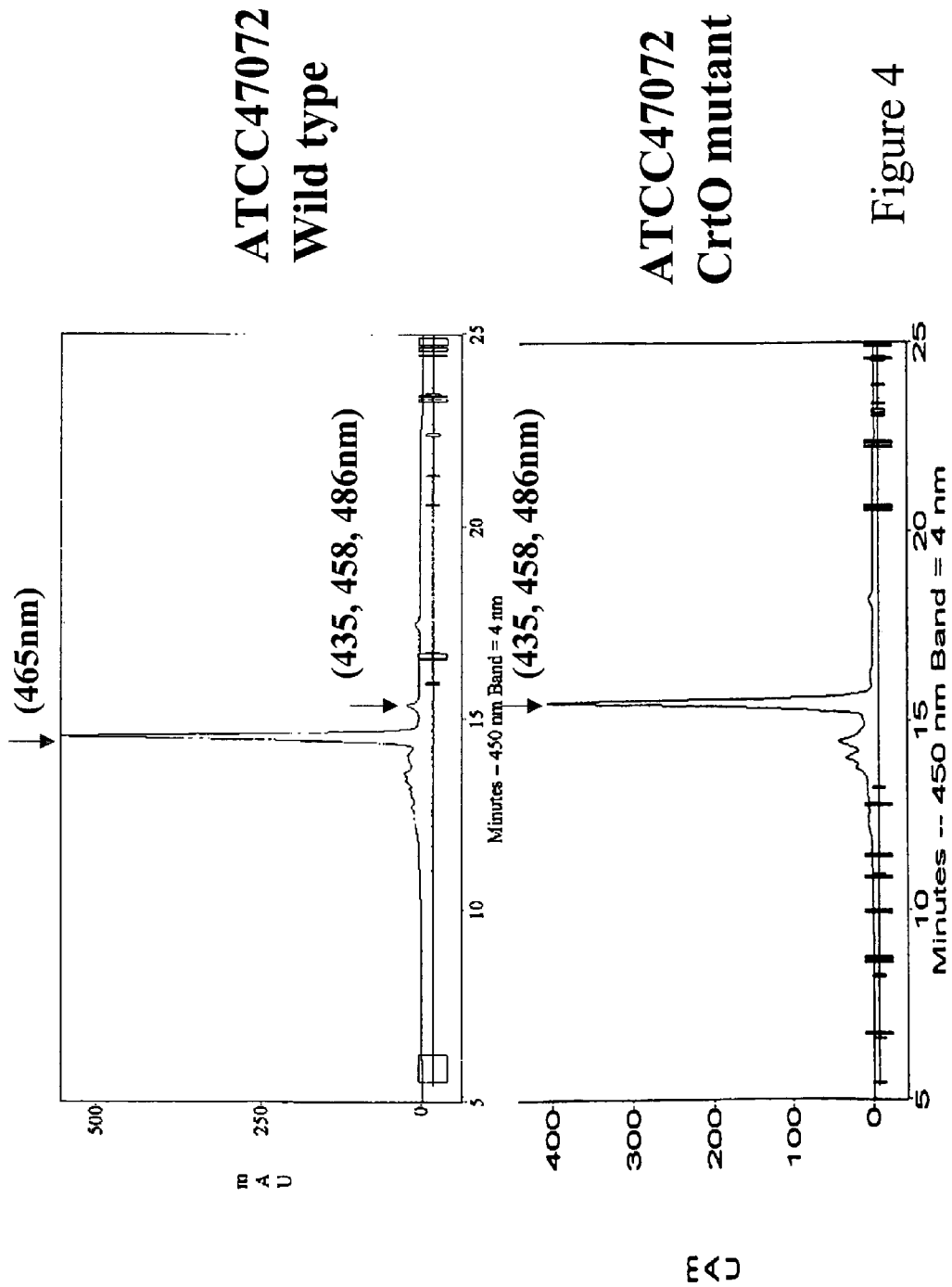

FIG. 4 describes the comparison of HPLC profiles of the carotenoids from wild type *Rhodococcus* ATCC 47072 and the CrtO mutant.

FIG. 5 describes HPLC analysis of the pigment from *E. coli* expressing crtO.

Figure 6:
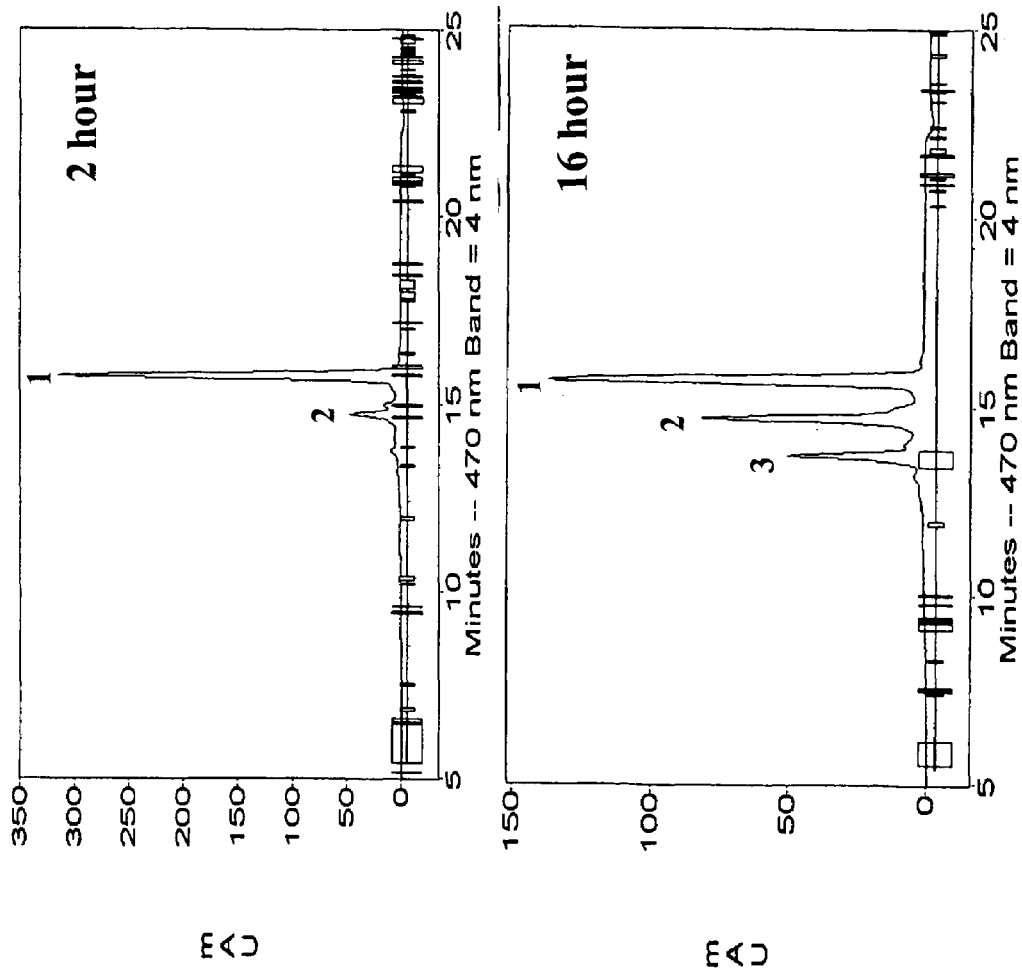

FIG. 6 describes HPLC analysis of the in vitro ketolase activity of CrtO from *Rhodococcus*.

The invention can be more fully understood from the following detailed description and the accompanying sequence descriptions, which form a part of this application.

The following sequences comply with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence encoding crtO gene from *Rhodococcus erythropolis* AN12 strain.

SEQ ID NO:2 is deduced amino acid sequence of crtO gene used in SEQ ID NO:1.

SEQ ID NO:3 is the nucleotide sequence encoding crtO gene from *Deinococcus radiodurans* R1 strain.

SEQ ID NO:4 is deduced amino acid sequence of crtO gene used in SEQ ID NO:3.

SEQ ID NO:5 is the nucleotide sequence of crtO gene from *Synechocystis* sp. PCC6803 strain.

SEQ ID NO:6 is deduced amino acid sequence of crtO gene used in SEQ ID NO:5.

SEQ ID NOs:7–12 are the amino acid sequences of conserved diagnostic motifs among CrtO enzymes described in SEQ ID NOs:2, 4, and 6.

SEQ ID NOs:13–25 are primer sequences.

SEQ ID NOs:26–31 are *Rhodococcus erythropolis* AN12 crtO motifs 1–6, respectively SEQ ID NOs:32–37 are *Deinococcus* crtO motifs 1–6, respectively, and SEQ ID NOs:38–43 are *Synechocystis* crtO motifs 1–6 respectively.

SEQ ID NOs:44–45 are oligonucleotide primers used to amplify the crt genes from *P. stewartii*.

SEQ ID NOs:46–47 are oligonucleotide primers used to amplify the *R. erythropolis* AN12 crtO gene.

DETAILED DESCRIPTION OF THE INVENTION

The present crtO gene and its expression product, a cyclic carotenoid ketolase, are useful for the creation of recombinant organisms that have the ability to produce cyclic ketocarotenoid compounds. Nucleic acid fragments encoding the above mentioned enzyme have been isolated from a strain of *Rhodococcus erythropolis* and identified by comparison to public databases containing nucleotide and protein sequences using the BLAST and FASTA algorithms well known to those skilled in the art. Motif analysis among three CrtO enzymes using MEME program has identified six conserved diagnostic motifs among CrtO enzymes from *Rhodococcus, Deinococcus* and *Synechocystis.*

The genes and gene products of the present invention may be used in a variety of ways for the production or regulation of cyclic ketocarotenoid compounds.

The microbial isoprenoid pathway is naturally a multi-product platform for production of compounds such as carotenoids, quinones, squalene, and vitamins. These natural products may be from 5 carbon units to more than 55 carbon units in chain length. There is a general practical utility for microbial isoprenoid production as these compounds are very difficult to make chemically (Nelis and Leenheer, *Appl. Bacteriol.* 70:181–191 (1991)).

In the case of *Rhodococcus erythropolis* the inherent capacity to produce carotenoids is particularly useful. Because *Rhodococcus* cells are resistant to many solvents and amenable to mixed phase process development, it is advantageous to use *Rhodococcus* strain as a production platform. *Rhodococcus* strains have been successfully used as a production hosts for the commercial production of other chemicals such as acrylamide.

The gene and gene sequences described herein enable one to incorporate the production of healthful carotenoids directly into the single cell protein product derived from *Rhodococcus erythropolis.* This aspect makes this strain or any bacterial strain into which these genes are incorporated a more desirable production host for animal feed due to the presence of carotenoids which are known to add desirable pigmentation and health benefits to the feed. Salmon and shrimp aquacultures are particularly useful applications for this invention as carotenoid pigmentation is critically important for the value of these organisms (F. Shahidi, J. A. Brown, Carotenoid pigments in seafood and aquaculture, *Critical Reviews in Food Science* 38(1):1–67 (1998)). Specifically, the ketocarotenoid astaxanthin, is a powerful antioxidant and has been reported to boost immune functions in humans and reduce carcinogenesis (Jyonouchi et al., *Nutr. Cancer* (1995) 23:171–183; Tanaka et al., *Cancer Res.* (1995) 55:4059–4064).

In this disclosure, a number of terms and abbreviations are used. The following definitions are provided.

"Open reading frame" is abbreviated ORF.

"Polymerase chain reaction" is abbreviated PCR.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "isoprenoid" or "terpenoid" refers to the compounds are any molecule derived from the isoprenoid pathway including 10 carbon terpenoids and their derivatives, such as carotenoids and xanthophylls.

The terms "*Rhodococcus erythropolis* AN12" or "AN12" will be used interchangeably and refer to the *Rhodococcus erythropolis* AN12 strain.

The term "*Rhodococcus erythropolis* ATCC 47072" or "ATCC 47072" will be used interchangeably and refers to the *Rhodococcus erythropolis* ATCC 47072 strain.

The term "carotenoid" refers to a compound composed of a polyene backbone which is condensed from five-carbon isoprene unit. Carotenoids can be acyclic or terminated with one (monocyclic) or two (bicyclic) cyclic end groups. The term "carotenoid" may include both carotenes and xanthophylls. A "carotene" refers to a hydrocarbon carotenoid. Carotene derivatives that contain one or more oxygen atoms, in the form of hydroxy-, methoxy-, oxo-, epoxy-, carboxy-, or aldehydic functional groups, or within glycosides, glycoside esters, or sulfates, are collectively known as "xanthophylls". Carotenoids that are particularly suitable in the present invention are monocyclic and bicyclic carotenoids.

The term "carotenoid ketolase" or "ketolase" or "cyclic carotenoid ketolase" refers to the group of enzymes that can add keto groups to the ionone ring of either monocyclic or bicyclic carotenoids.

The term "motif" refers to short conserved amino acid sequences found in a group of protein sequences. Motifs frequently form a recognition sequence or are highly conserved parts of domains. Motif may also refer to all localized homology regions, independent of their size. A motif descriptor could be used to describe the short sequence motifs, consisting of amino acid characters and other characters represent ambiguities and length insertions.

The term "diagnostic conserved motifs" or "conserved amino acid motifs" or "diagnostic motif" refers to amino acid sequences that are common among CrtO ketolase enzymes and the presence of which is diagnostic for cyclic carotenoid ketolase functionality.

The term "keto group" or "ketone group" will be used interchangeably and refers to a group in which a carbonyl group is bonded to two carbon atoms: $R_2C=O$ (neither R may be H).

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences.

For example, it is well known in the art that alterations in a gene which result in the production of a chemically equivalent amino acid at a given site, but do not effect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product.

In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1× SSC, 0.1% SDS, 65° C. and washed with 2×SSC, 0.1% SDS followed by 0.1×SSC, 0.1% SDS), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Most preferred are nucleic acid fragments that are at least 95% identical to the DNA sequence of the nucleic acid fragments reported herein.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis*

*Primer* (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant microbial polypeptides as set forth in SEQ ID NO's 2 and 7–12 The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 9928508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "altered biological activity" will refer to an activity, associated with a protein encoded by a microbial nucleotide sequence which can be measured by an assay method, where that activity is either greater than or less than the activity associated with the native microbial sequence. "Enhanced biological activity" refers to an altered activity that is greater than that associated with the native sequence. "Diminished biological activity" is an altered activity that is less than that associated with the native sequence.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). The term "MEME" refers to a software program used to identify the 6 conserved diagnostic motifs in a group of crtO sequences based on hidden Markov model (Timothy L. Bailey and Charles Elkan, *Fitting a mixture model by expectation maximization to discover motifs in biopolymers*, Proceedings of the Second International Conference on Intelligent Systems for Molecular Biology, pp. 28–36, AAAI Press, Menlo Park, Calif., 1994.) "MAST" (Timothy L. Bailey and Michael Gribskov, "Combining evidence using p-values: application to sequence homology searches" *Bioinformatics*, Vol. 14, pp. 48–54, 1998) is a program that takes the output from the MEME program and searches the identified motifs against the protein databases such as EMBL and SwissProt. Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The present invention provides a newly discovered crtO gene, isolated from *Rhodococcus* and encoding a cyclic carotenoid ketolase. The invention also provides the finding that a gene, previously identified as a phytoene dehydrogenase from *Deinococcus radiodurans* has cyclic carotenoid ketolase activity. The present sequences may be used in vitro and in vivo in recombinant hosts for the production of cyclic ketocarotenoids from monocyclic and bicyclic carotenoid compounds.

Comparison of the crtO nucleotide base and deduced amino acid sequences to public databases reveals that the most similar known sequences were about 35% identical to the amino acid sequence of reported herein over length of 532 amino acid using a Smith-Waterman alignment algorithm (W. R. Pearson, *Comput. Methods Genome Res., [Proc. Int. Symp.]* (1994), Meeting Date 1992, 111–20. Editor(s): Suhai, Sandor. Publisher: Plenum, New York, N.Y.). Accordingly preferred amino acid fragments are at least about 70%–80% identical to the sequences herein, more preferred amino acid sequences are at least about 80%–90% identical to the amino acid fragments reported herein and most preferred are nucleic acid fragments that are at least 95% identical to the amino acid fragments reported herein. Similarly, preferred crtO encoding nucleic acid sequences corresponding to the instant sequences are those encoding active proteins and which are at least 80% identical to the nucleic acid sequences of reported herein. More preferred crtO nucleic acid fragments are at least 90% identical to the sequences herein. Most preferred are crtO nucleic acid fragments that are at least 95% identical to the nucleic acid fragments reported herein.

Motif analysis was performed on three crtO genes. The analysis compared the amino acid sequences of the CrtO enzyme isolated from *Rhodococcus* AN12 (SEQ ID NO:2), the CrtO enzyme isolated from *Deinococcus* (SEQ ID NO:4) and the known CrtO enzyme isolated from *Synechocystis* (SEQ ID NO:6). The results of this analysis identified six highly conserved diagnostic motifs present in all three enzymes (FIG. 3). Those motif consensus sequences are set forth in SEQ ID NOs:7–12. It is contemplated that the presence of all of these motifs in a single polypeptide is diagnostic for the CrtO, ketolase functionality. Accordingly the invention provides an isolated nucleic acid molecule encoding a carotenoid ketolase enzyme, the enzyme having at least 70% identity based on the Smith-Waterman method of alignment to all of the amino acid sequences defining CrtO diagnostic motifs as set forth in SEQ ID NOs:7–12. Similarly the invention provides a polypeptide having carotenoid ketolase activity, the polypeptide having at least 70% identity based on the Smith-Waterman method of alignment to all of the amino acid sequences defining CrtO diagnostic motifs as set forth in SEQ ID NOs:7–12. The foregoing notwithstanding, the invention expressly excludes the *Synechocystis* sp. PCC6803 crtO gene and enzyme as described by Fernández-González et al. (*J. of Biol. Chem.* (1997) 272;9728–9733) and as set forth in SEQ ID NO:5 and 6 respectively.

Isolation of Homologs

The nucleic acid fragments of the instant invention may be used to isolate genes encoding homologous proteins from the same or other microbial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202), ligase chain reaction (LCR), Tabor, S. et al., *Proc. Acad. Sci.* USA 82, 1074, (1985)) or strand displacement amplification (SDA, Walker, et al., *Proc. Natl. Acad. Sci. U.S.A.,* 89, 392, (1992)).

For example, genes encoding similar proteins or polypetides to those of the instant invention could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, end-labeling techniques, or RNA probes using available in vitro transcription systems. In addition, specific primers can be designed and used to amplify a part of or the full-length of the instant sequences. The resulting amplification products can be labeled directly during amplification reactions or labeled after amplification reactions, and used as probes to isolate full length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33–50 IRL Press, Herndon, Va.); Rychlik, W. (1993) In White, B. A. (ed.), *Methods in Molecular Biology*, Vol. 15, pages 31–39, PCR Protocols: Current Methods and Applications. Humania Press, Inc., Totowa, N.J.)

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor of a eukaryotic gene. In the case of microbial genes which lack poly adenylated mRNA, random primers may be used. Random primers may also be useful for amplifcation from DNA.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *PNAS USA* 86:5673 (1989); Loh et al., *Science* 243:217 (1989)).

Alternatively the instant sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature [Van Ness and Chen (1991) *Nucl. Acids Res.* 19:5143–5151]. Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening DNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen DNA expression libraries to isolate full-length DNA clones of interest (Lerner, R. A. *Adv. Immunol.* 36:1 (1984); Maniatis).

Recombinant Expression—Microbial

The gene and gene product of the instant sequences may be produced in heterologous host cells, particularly in the cells of microbial hosts. Expression in recombinant microbial hosts may be useful for the expression of various pathway intermediates, for the modulation of pathways already existing in the host, or for the synthesis of new products heretofore not possible using the host.

Preferred heterologous host cells for expression of the instant genes and nucleic acid fragments are microbial hosts that can be found broadly within the fungal or bacterial families and which grow over a wide range of temperature, pH values, and solvent tolerances. For example, it is contemplated that any of bacteria, yeast, and filamentous fungi will be suitable hosts for expression of the present nucleic acid fragments. Because of transcription, translation and the protein biosynthetic apparatus is the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols, saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strains include but are not limited to bacterial, fungal or yeast species such as *Aspergillus, Trichoderma, Saccharomyces, Pichia, Candida, Hansenula,* or bacterial species such as *Salmonella, Bacillus, Acinetobacter, Zymomonas, Agrobacterium, Erythrobacter Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella,* and *Myxococcus*.

Microbial expression systems and expression vectors containing regulatory sequences that direct high level expression of foreign proteins are well known to those skilled in the art. Any of these could be used to construct chimeric genes for expression of present ketolases. These chimeric genes could then be introduced into appropriate microorganisms via transformation to provide high level expression of the enzymes Accordingly it is expected, for example, that introduction of chimeric genes encoding the instant bacterial enzymes under the control of the appropriate promoters, will demonstrate increased or altered cyclic carotenoid production. It is contemplated that it will be useful to express the instant genes both in natural host cells as well as heterologous host. Introduction of the present CrtO genes into native host will result in altered levels of existing carotenoid production. Additionally, the instant genes may also be introduced into non-native host bacteria where the existing carotenoid pathway may be manipulated.

Specific ketocarotenoids that will be produced by the present invention include but are not limited to, canthaxanthin, astaxanthin, adonixanthin, adonirubin, echinenone, 3-hydroxyechinenone, 3'-hydroxyechinenone, 4-keto-gamma-carotene, 4-keto-rubixanthin, 4-keto-torulene, 3-hydroxy-4-keto-torulene, deoxyflexixanthin, and myxobactone. Of particular interest is the production of astaxanthin 4-keto-rubixanthin, the synthesis of which is shown in FIG. 1. The specific substrate for the present CrtO enzyme is a monocyclic or bicyclic carotenoid. Cyclic carotenoids are well known in the art and available commercially. Preferred in the present invention as CrtO ketolase substrates are cyclic carotenoid that include but are not limited to β-Carotene, γ-carotene, zeaxanthin, rubixanthin, echinenone, and torulene.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*. Promoters such as the chloramphenical resistance gene promoter may be useful for expression in *Rhodococcus*.

Termination control regions may also be derived from various genes native to the preferred hosts. Optionally, a termination site may be unnecessary, however, it is most preferred if included.

Knowledge of the sequence of the present gene will be useful in manipulating the carotenoid biosynthetic pathways in any organism having such a pathway and particularly in *Rhodococcus*. Methods of manipulating genetic pathways are common and well known in the art. Selected genes in a particularly pathway may be upregulated or down regulated by variety of methods. Additionally, competing pathways organism may be eliminated or sublimated by gene disruption and similar techniques.

Once a key genetic pathway has been identified and sequenced specific genes may be upregulated to increase the output of the pathway. For example, additional copies of the targeted genes may be introduced into the host cell on multicopy plasmids such as pBR322. Alternatively the target genes may be modified so as to be under the control of non-native promoters. Where it is desired that-a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (see, Kmiec, U.S. Pat. No. 5,565,350; Zarling et al., PCT/US93/03868).

Alternatively it may be necessary to reduce or eliminate the expression of certain genes in the target pathway or in competing pathways that may serve as competing sinks for energy or carbon. Methods of down-regulating genes for this purpose have been explored. Where sequence of the gene to be disrupted is known, one of the most effective methods gene down regulation is targeted gene disruption where foreign DNA is inserted into a structural gene so as to disrupt transcription. This can be effected by the creation of genetic cassettes comprising the DNA to be inserted (often a genetic marker) flanked by sequence having a high degree of homology to a portion of the gene to be disrupted. Introduction of the cassette into the host cell results in insertion of the foreign DNA into the structural gene via the native DNA replication mechanisms of the cell. (See for example Hamilton et al. (1989) *J. Bacteriol.* 171:4617–4622, Balbas et al. (1993) *Gene* 136:211–213, Gueldener et al. (1996) *Nucleic Acids Res.* 24:2519–2524, and Smith et al. (1996) *Methods Mol. Cell. Biol.* 5:270–277.)

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA which encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to a UV radiation and then screened for the desired phenotype. Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992).

Another non-specific method of gene disruption is the use of transposoable elements or transposons. Transposons are genetic elements that insert randomly in DNA but can be latter retrieved on the basis of sequence to determine where the insertion has occurred. Both in vivo and in vitro transposition methods are known. Both methods involve the use of a transposable element in combination with a transposase enzyme. When the transposable element or transposon, is contacted with a nucleic acid fragment in the presence of the transposase, the transposable element will randomly insert into the nucleic acid fragment. The technique is useful for random mutageneis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element.

Industrial Production

Where commercial production of cyclic ketocarotenoid compounds is desired, using the present crtO genes, a variety of culture methodologies may be applied. For example, large-scale production of a specific gene product, overexpressed from a recombinant microbial host may be produced by both batch or continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the fed-batch system. Fed-batch culture processes are also suitable in the present invention and comprise a typical batch system with the exception that the substrate is added in increments as the culture progresses. Fed-batch systems are useful when catabolite repression is apt to inhibit the metabolism of the cells and where it is desirable to have limited amounts of substrate in the media. Measurement of the actual substrate concentration in fed-batch systems is difficult and is therefore estimated on the basis of the changes of measurable factors such as pH, dissolved oxygen and the partial pressure of waste gases such as $CO_2$. Batch and fed-batch culturing methods are common and well known in the art and examples may be found in Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992), herein incorporated by reference.

Commercial production of cyclic ketocarotenoids may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, methane or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415–32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485–489 (1990)). Hence it is contemplated that the source of carbon utilized in the present invention may encompass a wide variety of carbon containing substrates and will only be limited by the choice of organism.

Recombinant Expression—Plants

Plants and algae are also known to produce carotenoid compounds. The nucleic acid fragments of the instant invention may be used to create transgenic plants having the ability to express the microbial protein. Preferred plant hosts will be any variety that will support a high production level of the instant proteins. Suitable green plants will include but are not limited to soybean, rapeseed (*Brassica napus, B. campestris*), pepper, sunflower (*Helianthus annus*), cotton (*Gossypium hirsutum*), corn, tobacco (*Nicotiana tabacum*), alfalfa (*Medicago sativa*), wheat (*Triticum* sp), barley (*Hordeum vulgare*), oats (*Avena sativa, L*), sorghum (*Sorghum bicolor*), rice (*Oryza sativa*), *Arabidopsis*, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Algal species include but not limited to commercially significant hosts such as *Spirulina, Haemotacoccus*, and *Dunalliela*. Production of the carotenoid compounds may be accomplished by first constructing chimeric genes of present invention in which the coding region are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with the genetic sequences or the present invention should be capable of promoting expression of the present gene product. High level plant promoters that may be used in this invention include the promoter of the small subunit (ss) of the ribulose-1,5-bisphosphate carboxylase from example from soybean (Berry-Lowe et al., *J. Molecular and App. Gen.*, 1:483–498 1982)), and the promoter of the chlorophyll a/b binding protein. These two promoters are known to be light-induced in plant cells (see, for example, *Genetic Engineering of Plants, an Agricultural Perspective*, A. Cashmore, Plenum, N.Y. (1983), pages 29–38; Coruzzi, G. et al., *The Journal of Biological Chemistry*, 258:1399 (1983), and Dunsmuir, P. et al., *Journal of Molecular and Applied Genetics*, 2:285 (1983)).

Plasmid vectors comprising the instant chimeric genes can then constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA blots (Southern, *J. Mol. Biol.* 98, 503, (1975)). Northern analysis of mRNA expression (Kroczek, *J. Chromatogr. Biomed. Appl.*, 618 (1–2) (1993) 133–145), Western analysis of protein expression, or phenotypic analysis.

For some applications it will be useful to direct the instant proteins to different cellular compartments. It is thus envisioned that the chimeric genes described above may be further supplemented by altering the coding sequences to encode enzymes with appropriate intracellular targeting sequences such as transit sequences (Keegstra, K., *Cell* 56:247–253 (1989)), signal sequences or sequences encoding endoplasmic reticulum localization (Chrispeels, J. J., *Ann. Rev. Plant Phys. Plant Mol. Biol.* 42:21–53 (1991)), or nuclear localization signals (Raikhel, N. *Plant Phys.* 100: 1627–1632 (1992)) added and/or with targeting sequences that are already present removed. While the references cited give examples of each of these, the list is not exhaustive and more targeting signals of utility may be discovered in the future that are useful in the invention.

Protein Engineering

It is contemplated that the present nucleotides may be used to produce gene products having enhanced or altered activity. Various methods are known for mutating a native gene sequence to produce a gene product with altered or enhanced activity including but not limited to error-prone PCR (Melnikov et al., *Nucleic Acids Research*, (Feb. 15, 1999) Vol. 27, No. 4, pp. 1056–1062); site-directed mutagenesis (Coombs et al., *Proteins* (1998), 259–311, 1 plate. Editor(s): Angeletti, Ruth Hogue. Publisher: Academic, San Diego, Calif.) and "gene shuffling" (U.S. Pat. Nos. 5,605,793; 5,811,238; 5,830,721; and 5,837,458, incorporated herein by reference).

The method of gene shuffling is particularly attractive due to its facile implementation, and high rate of mutagenesis and ease of screening. The process of gene shuffling involves the restriction endonuclease cleavage of a gene of interest into fragments of specific size in the presence of additional populations of DNA regions of both similarity to or difference to the gene of interest. This pool of fragments will then be denatured and reannealed to create a mutated gene. The mutated gene is then screened for altered activity.

The instant microbial sequences of the present invention may be mutated and screened for altered or enhanced activity by this method. The sequences should be double stranded and can be of various lengths ranging form 50 bp to 10 kb. The sequences may be randomly digested into fragments ranging from about 10 bp to 1000 bp, using restriction endonucleases well known in the art (Maniatis supra). In addition to the instant microbial sequences, populations of fragments that are hybridizable to all or portions of the microbial sequence may be added. Similarly, a population of fragments which are not hybridizable to the instant sequence may also be added. Typically these additional fragment populations are added in about a 10 to 20 fold excess by weight as compared to the total nucleic acid. Generally if this process is followed the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double stranded nucleic acid. Preferably the temperature is from 80° C. to 100° C. The nucleic acid fragments may be reannealed by cooling. Preferably the temperature is from 20° C. to 75° C. Renaturation can be accelerated by the addition of polyethylene glycol ("PEG") or salt. A suitable salt concentration may range from 0 mM to 200 mM. The annealed nucleic acid fragments are then incubated in the presence of a nucleic acid polymerase and dNTP's (i.e., dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from 2 to 50 times, more preferably the sequence is repeated from 10 to 40 times. The resulting nucleic acid is a larger double-stranded polynucleotide ranging from about 50 bp to about 100 kb and may be screened for expression and altered activity by standard cloning and expression protocol. (Manatis supra).

Furthermore, a hybrid protein can be assembled by fusion of functional domains using the gene shuffling (exon shuffling) method (Nixon et al., PNAS, 94:1069–1073 (1997)). The functional domain of the instant gene can be combined with the functional domain of other genes to create novel enzymes with desired catalytic function. A hybrid enzyme may be constructed using PCR overlap extension method and cloned into the various expression vectors using the techniques well known to those skilled in art.

DESCRIPTION OF THE PREFERRED EMBODIMENTS

The original environmental sample containing *Rhodococcus erythropolis* AN12 strain was obtained from a wastewater treatment facility. One ml of activated sludge was inoculated directly into 10 ml of S12 medium. Aniline was used as the sole source of carbon and energy. The culture was maintained by addition of 100 ppm aniline every 2–3 days. The culture was diluted (1:100 dilution) every 14 days. Bacteria that utilize aniline as a sole source of carbon and energy were further isolated and purified on S12 agar. Aniline (5 μL) was placed on the interior of each culture dish lid.

When 16s rRNA gene of AN12 was sequenced and compared to other 16s rRNA sequence in the GenBank sequence database, 16s rRNA gene of AN12 strain has at least 98% similarity to the 16s rRNA gene sequences of high G+C gram positive *Rhodococcus* genus.

Genomic nucleotide sequences have been isolated from *Rhodococcus erythropolis* AN12 strain and compared to genes from existing database. There were two ORFs that shared homology with two different putative phytoene dehydrogenase. The gene in ORF 1 was designated as crtO and the other was designated as crtI. Two genes shared very little homology with each other (24% identity). Sequence in ORF 1 (SEQ ID NO:1) has 35% identity with a gene suspected to be a phytoene dehydrogenase from *Deinococcus radiodurans*. CrtI, but not CrtO, was determined to be a dehydrogenase since the crtI mutant with intact crtO exhibited the phytoene dehydrogenase knockout phenotype. The present invention shows that crtO (ORF1) encodes a ketolase that adds ketone groups to the β-ionone rings of the cyclic carotenoids to produce ketocarotenoids.

Two types of carotenoid ketolases (the CrtW type and the CrtO type) have been reported (Kajiwara, et al, 1995, *Plant Mol. Biol.* 29:343–352; Fernández-González, et al., *J. Biol. Chem.*, 1997, 272:9728–9733). All CrtW enzymes are symmetric 2-ring ketolases. The CrtO isolated herein from AN12 and *Deinococcus* are symmetric 2-ring ketolases, similar to CrtW.

FIG. 2 shows a phylogenetic tree analysis of all the reported ketolases in the literature. The CrtW type and the CrtO type of ketolases clearly belong to two different branches of the phylogenetic tree. The CrtW type ketolase symmetrically adds a ketone group to both β-ionone rings of β-carotene to generate canthaxanthin. Only one CrtO type ketolase has been previously reported in the literature (Fernández-González, et al., *J. Biol. Chem.*, 1997, 272: 9728–9733). This CrtO was isolated from *Synechocystis* sp. PCC6803 and was shown to be a new type of asymmetrically acting β-carotene ketolase that introduces a keto group to only one of the β-ionone rings of β-carotene to generate echinenone. Interesting, the *Synechocystis* CrtO (slr0088) has significant homology to the bacterial phytoene dehydrogenases but showed no such activity biochemically. The CrtO gene of the present invention was isolated from *Rhodococcus erythropolis* AN12 and is 532 amino acids in length. The most similar sequence to the *Rhodococcus* crtO as determined by the BLAST program (Basic Local Alignment Search Tool; Altschul, S. F., et al., (1993) *J. Mol. Biol.* 215:403–410) was to the 511 amino acid protein isolated from *Deinococcus* with the putative function of phytoene dehydrogenase DR0093. Applicants have demonstrated that the function of DR0093 of *Deinococcus* is also a carotenoid ketolase and not a phytoene dehydrogenase, as previously reported.

The second closest alignment generated from the BLAST search to the *Rhodococcus* CrtO was to a *Synechocystis* hypothetical protein (slr0088) having 542 amino acids, that was later confirmed to be a CrtO ketolase (Fernández-González, et al., *J. Biol. Chem.*, 1997, 272:9728–9733). The CrtO from *Rhodococcus* has 35% amino acid identity and 64% similarity with the CrtO from *Synechocystis*. It shared very little sequence homology with the CrtW type of enzymes. Phylogenetic analysis grouped the *Rhodococcus* CrtO, the *Deinococcus* CrtO and the *Synechocystis* CrtO together in a separate branch, separate from all the CrtW enzymes (FIG. 2). The CrtO designation of the *Rhodococcus* ORF was based on the shared sequence homology with the *Synechocystis* CrtO.

Motif analysis was performed using MEME program (Timothy L. Bailey and Charles Elkan, *Fitting a mixture model by expectation maximization to discover motifs in biopolymers*, Proceedings of the Second International Conference on Intelligent Systems for Molecular Biology, pp. 28–36, AAAI Press, Menlo Park, Calif., 1994) with the three CrtO enzymes from *Rhodococcus, Deinococcus* or *Synechocystis* (FIG. 3). Six conserved motifs were identified in each of the three CrtO enzymes. The location of the motifs is also conserved in the CrtO enzymes compared. The consensus sequence of the motifs was used to search the EMBL and SwissProt databases using the MAST program (Bailey and Gribskov supra). No other proteins in the public databases were found to have all six motifs, which makes the presence of these three motifs together diagnostic of the CrtO ketolase function. The most closely related proteins based on the motif search were several phytoene dehydrogenase CrtI enzymes, which had only two or three of the motifs. The presence and location of the six motifs may be a signature for the CrtO type of carotenoid ketolases.

When the crtO gene was disrupted by mutation, the colonies of CrtO mutants were yellow in comparison to the pink color in the strain with the intact crtO gene. The carotenoids were extracted from mutant colonies and analyzed by HPLC (FIG. 4). Pigments from CrtO mutant colonies lacked the major peak that is present in the colonies with intact crtO gene suggesting that the CrtO enzyme is involved in the conversion of yellow form of carotenoids to a pink form of the carotenoids. This finding was additionally confirmed when it was shown that when the keto group of major carotenoid from the wild-type strain was chemically reduced, it changed color from pink to yellow.

The major carotenoid in the CrtO mutant was purified and further examined. The molecular weight of the major carotenoid in the mutant CrtO strain was determined to be 536 Dalton using MALDI-MS. The molecular weight of the major and minor carotenoids (minor peak being identical to the major peak of CrtO mutant) in the wild type ATCC 47072 was determined to be 550 Dalton and 536 Dalton, respectively suggesting that the difference of 14 Daltons is due to one keto-group addition by the native CrtO.

The *E. coli* genome does not contain any crt genes, thus *E. coli* cell extracts do not contain carotenoid ketolase that can use β-carotene as a substrate. The full length crtO gene isolated from *Rhodococcus* AN12 was cloned into *E. coli* (Example 7). When the *E. coli* host synthesized β-carotene in vivo from a cloned *P. stewartii* crtEXYIB cluster, expression of crtO converted β-carotene to canthaxanthin (92%) and echinenone (6%). The β-carotene compound was also added in vitro to crude cell extract of *E. coli* which expressed CrtO (Example 8). HPLC analysis of 2 hr and 16 hr reaction mixtures was performed to identify reaction intermediates as well as reaction products produced as a result of the CrtO enzyme activity. The 2 hr reaction mixture contained only one additional peak. At this time point, echinenone was the only intermediate produced and no canthaxanthin was detected. Longer incubation times resulted in increased levels of echinenone which was then converted to canthaxanthin, which is the final product representing the addition of two ketone groups (Table 2). This in vitro assay data confirmed that crtO encodes a ketolase, which converts β-carotene into canthaxanthin (containing two ketone groups) via echinenone (containing one ketone group) as the intermediate. This symmetric ketolase activity of *Rhodococcus* AN12 CrtO is different from that which has been reported "for the asymmetric function of *Synechocystis* CrtO.

Although the *Deinococcus* Gene DR0093 is currently annotated as a probable phytoene dehydrogenase in the database, it shares close homology with the *Rhodococcus* crtO gene. The function of DR0093 was investigated to determine if it encoded a carotenoid ketolase or a phytoene dehydrogenase. The DR0093 gene was expressed in *E. coli* essentially and the in vitro enzyme assays determined that the CrtO of *Deinococcus* behaved in a similar fashion to that of the *Rhodococcus* CrtO, in that it added two ketone groups to β-carotene to form canthaxanthin via echinenone, thus confirming its carotenoid ketolase activity.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories/BD Diagnostics (Sparks, Md.), Promega (Madison, Wis.), New England Biolabs (Beverly, Mass.), GIBCO/BRL Life Technologies (Carlsbad, Calif.), or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.). Where the GCG program "Pileup" was used the gap creation default value of 12, and the gap extension default value of 4 were used. Where the CGC "Gap" or "Bestfit" programs were used the default gap creation penalty of 50 and the default gap extension penalty of 3 were used. Multiple alignments were created using the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). In any case where program parameters were not prompted for, in these or any other programs, default values were used.

The meaning of abbreviations is as follows: "h" means hour(s), "min" means minute(s), "sec" means second(s), "d" means day(s), "ml" means milliliters, "L" means liters.

Example 1

Isolation and Characterization of Strain AN12

Example 1 describes the isolation of strain AN12 of *Rhodococcus erythropolis* on the basis of being able to grow on aniline as the sole source of carbon and energy. Analysis of a 16S rRNA gene sequence indicated that strain AN12 was related to high G+C Gram positive bacteria belonging to the genus *Rhodococcus*.

Bacteria that grew on aniline were isolated from an enrichment culture. The enrichment culture was established by inoculating 1 ml of activated sludge into 10 ml of S12 medium (10 mM ammonium sulfate, 50 mM potassium phosphate buffer (pH 7.0), 2 mM $MgCl_2$, 0.7 mM $CaCl_2$, 50 µM $MnCl_2$, 1 µM $FeCl_3$, 1 µM $ZnCl_3$, 1.72 µM $CuSO_4$, 2.53 µM $COCl_2$, 2.42 µM $Na_2MoO_2$, and 0.0001% $FeSO_4$) in a 125 ml screw cap Erlenmeyer flask. The activated sludge was obtained from a wastewater treatment facility. The enrichment culture was supplemented with 100 ppm aniline added directly to the culture medium and was incubated at 25° C. with reciprocal shaking. The enrichment culture was maintained by adding 100 ppm of aniline every 2–3 days. The culture was diluted every 14 days by replacing 9.9 ml of the culture with the same volume of S12 medium. Bacteria that utilized aniline as a sole source of carbon and energy were isolated by spreading samples of the enrichment culture onto S12 agar. Aniline (5 µL) was placed on the interior of each petri dish lid. The petri dishes were sealed with parafilm and incubated upside down at room temperature (approximately 25° C.). Representative bacterial colonies were then tested for the ability to use aniline as a sole source of carbon and energy. Colonies were transferred from the original S12 agar plates used for initial isolation to new S12 agar plates and supplied with aniline on the interior of each petri dish lid. The petri dishes were sealed with parafilm and incubated upside down at room temperature (approximately 25° C.).

The 16S rRNA genes of each isolate were amplified by PCR and analyzed as follows. Each isolate was grown on R2A agar (Difco Laboratories). Several colonies from a culture plate were suspended in 100 µl of water. The mixture was frozen and then thawed once. The 16S rRNA gene sequences were amplified by PCR using a commercial kit according to the manufacturer's instructions (Perkin Elmer, Norwalk, Conn.) with primers HK12 (5'-GAGTTTGATC-CTGGCTCAG-3') (SEQ ID NO:23) and HK13 (5'-TACCT-TGTTACGACTT-3') (SEQ ID NO:24). PCR was performed in a Perkin Elmer GeneAmp 9600 (Norwalk, Conn.). The samples were incubated for 5 min at 94° C. and then cycled 35 times at 94° C. for 30 sec, 55° C. for 1 min, and 72° C. for 1 min. The amplified 16S rRNA genes were purified using a commercial kit according to the manufacturer's instructions (QIAquick PCR Purification Kit, Qiagen, Valencia, Calif.) and sequenced on an automated ABI sequencer. The sequencing reactions were initiated with primers HK12, HK13, and HK14 (5'-GTGCCAG-CAGYMGCGGT-3') (SEQ ID NO:25, where Y=C or T, M=A or C). The 16S rRNA gene sequence of each isolate was used as the query sequence for a BLAST search [Altschul, et al., *Nucleic Acids Res.* 25:3389–3402(1997)] of GenBank for similar sequences.

A 16S rRNA gene of strain AN12 was sequenced and compared to other 16S rRNA sequences in the GenBank sequence database. The 16S rRNA gene sequence from strain AN12 was at least 98% similar to the 16S rRNA gene sequences of high G+C Gram positive bacteria belonging to the genus *Rhodococcus*.

Example 2

Preparation of Genomic DNA for Sequencing and Sequence Generation

Genomic DNA preparation. *Rhodococcus erythropolis* AN12 was grown in 25 mL NBYE medium (0.8% nutrient broth, 0.5% yeast extract, 0.05% Tween 80) till mid-log phase at 37° C. with aeration. Bacterial cells were centrifuged at 4,000 g for 30 min at 4° C. The cell pellet was washed once with 20 ml 50 mM $Na_2CO_3$ containing 1M KCl (pH 10) and then with 20 ml 50 mM NaOAc (pH 5). The cell pellet was gently resuspended in 5 ml of 50 mM Tris-10 mM EDTA (pH 8) and lysozyme was added to a final concentration of 2 mg/mL. The suspension was incubated at 37° C. for 2 h. Sodium dodecyl sulfate was then added to a final concentration of 1% and proteinase K was added to 100 µg/ml final concentration. The suspension was incubated at 55° C. for 5 h. The suspension became clear and the clear lysate was extracted with equal volume of phenol:chloroform:isoamyl alcohol (25:24:1). After centrifuging at 17,000 g for 20 min, the aqueous phase was carefully removed and transferred to a new tube. Two volumes of ethanol were added and the DNA was gently spooled with a sealed glass pasteur pipet. The DNA was dipped into a tube containing 70% ethanol, then air dried. After air drying, DNA was resuspended in 400 µl of TE (10 mM Tris-1 mM EDTA, pH 8) with RNaseA (100 µg/mL) and stored at 4° C.

Library construction. 200 to 500 µg of chromosomal DNA was resuspended in a solution of 300 mM sodium acetate, 10 mM Tris-HCl, 1 mM Na-EDTA, and 30% glycerol, and sheared at 12 psi for 60 sec in an Aeromist Downdraft Nebulizer chamber (IBI Medical products, Chicago, Ill.). The DNA was precipitated, resuspended and treated with Bal31 nuclease (New England Biolabs, Beverly, Mass.). After size fractionation by 0.8% agarose gel electrophoresis, a fraction (2.0 kb, or 5.0 kb) was excised, cleaned and a two-step ligation procedure was used to produce a high titer library with greater than 99% single inserts.

Sequencing. A shotgun sequencing strategy approach was adopted for the sequencing of the whole microbial genome (Fleischmann, Robert et al., Whole-Genome Random sequencing and assembly of *Haemophilus influenzae* Rd *Science,* 269:1995).

Sequence was generated on an ABI Automatic sequencer using dye terminator technology (U.S. Pat. No. 5,366,860; EP 272007) using a combination of vector and insert-specific primers. Sequence editing was performed in either DNAStar (DNA Star Inc., Madison, Wis.) or the Wisconsin GCG program (Wisconsin Package Version 9.0, Genetics Computer Group (GCG), Madison, Wis.) and the CONSED package (version 7.0). All sequences represent coverage at least two times in both directions.

Example 3

Sequence Analysis of the *Rhodococcus* AN12 CrtO

Two ORF's were identified in the genomic sequence of *Rhodococcus erythropolis* AN12 which shared homology to two different phytoene dehydrogenases. One ORF was designated CrtI and had the highest homology (45% identity, 56% similarity) to a putative phytoene dehydrogenase from *Streptomyces coelicolor* A3(2). The other ORF (originally designated as CrtI2, now as CrtO) had the highest homology (35% identity, 50% similarity; White O. et al *Science* 286 (5444), 1571–1577 (1999)) to a probable phytoene dehydrogenase DR0093 from *Deinococcus radiodurans*.

CrtI and CrtO of AN12 shared very little homology between each other (24% identity and 36% similarity in the 257 amino acid long N terminal half of the molecule which contains the FAD domain; no homology in the C terminal half of the molecule which contains the transmembrane substrate binding domain). CrtO was not a redundant phytoene dehydrogenase since the CrtI mutant with the intact CrtO exhibited a phytoene dehydrogenase knockout phenotype.

The data presented below confirms that the CrtO gene encodes a ketolase that adds ketone groups to the β-ionone rings of the cyclic carotenoids to produce ketocarotenoids.

Two types of carotenoid ketolases (the CrtW type and the CrtO type) have been reported. FIG. 2 shows a phylogenetic tree analysis of all the reported ketolases in the literature. The CrtW type and the CrtO type of ketolases clearly belong to two different branches of the phylogenetic tree. The CrtW type of ketolases symmetrically adds ketone groups to both β-ionone rings of β-carotene to generate canthaxanthin. These are clustered into two sub-groups, one group containing four enzymes from bacterial sources and one group containing two enzymes isolated from algae. The bacterial CrtW has 242 or 258 amino acids. The algal CrtW has 320 or 329 amino acids. The bacterial group and algal group of CrtW enzymes are homologous to each other. Only one other ketolase has been reported in the literature (Fernandez-Gonzalez, et al, *J. Biol. Chem.,* 1997, 272:9728). This CrtO is isolated from *Synechocystis* sp. PCC6803 and has been shown to be an asymmetrically acting β-carotene ketolase that introduces a ketone group to only one of the β-ionone rings of β-carotene to generate echinenone. It has 542 amino acids, which is considerably larger than the CrtW enzymes, and shares no homology with any of the CrtW enzymes. It is interesting that the *Synechocystis* CrtO (slr0088) is also similar to bacterial phytoene dehydrogenases but showed no such activity experimentally. The CrtO identified from *Rhodococcus erythropolis* AN12 is 532 amino acids in length. The closest homology to this sequence identified using a BLAST algorithm search or public databases was to the 511 amino acid *Deinococcus* gene (DR0093), putatively identified as a phytoene dehydrogenase. The function of DR0093 of *Deinococcus* has also demonstrated to be a carotenoid ketolase in this application.

The second highest homology which resulted from the BLAST search was to a *Synechocystis* hypothetical protein (slr0088) which has been confirmed as a CrtO ketolase (Fernandez-Gonzalez, et al, *J. Biol. Chem.,* 1997, 272:9728). The CrtO from *Rhodococcus* has 33% amino acid identity and 64% similarity with the CrtO from *Synechocystis*. Like *Synechocystis* CrtO, it also shares very little sequence resemblance to the CrtW type of enzymes. The phylogenetic analysis (FIG. 2) grouped the *Rhodococcus* CrtO, the *Deinococcus* CrtO and the *Synechocystis* CrtO together in a separate branch from all the CrtW enzymes. The CrtO designation of the *Rhodococcus* ORF was based on the shared sequence homology with the *Synechocystis* CrtO.

Motif analysis was performed using MEME program with the three CrtO enzymes from *Rhodococcus, Deinococcus* or *Synechocystis* (FIG. 3). Six conserved motifs were identified in each of the three CrtO enzymes. Four of the motifs were located at the amino terminal half of the proteins, and two were located close to the carboxyl end of the proteins. The location of the motifs is also conserved in the three CrtO enzymes. The six motifs common to the CrtO enzymes could not be found in the CrtW enzymes, and vice versa, the four conserved regions previously identified in the alignment of CrtW enzymes (Kajiwara, et al, 1995, *Plant Mol. Biol.* 29:343–352) are not present in the CrtO enzymes. Motif analysis further supports the finding that CrtO enzymes and CrtW enzymes are not homologous at the sequence level, although their functions may be similar.

The consensus sequence generated by alignment of the motifs was used to search the EMBL and SwissProt databases using the MAST program (Bailey and Gribskov supra). No other proteins in the databases have all six motifs as the three CrtO enzymes. The top hits from the MAST were several phytoene dehydrogenase CrtI enzymes, which had only two or three of the motifs. Presence and location of the six motifs may be a signature for the CrtO type of carotenoid ketolases.

Example 4

Analysis of Carotenoid Pigments in the *Rhodococcus* CrtO Mutant

A *Rhodococcus* CrtO disruption mutant was generated by homologous recombination in ATCC 47072. PCR primers AN12_I2_F (5'-CCATGGTCTGCGCACCTCATGATCCGA-3': SEQ ID NO:13) and AN12_I2_R (5'-CCATGGAATGAAGCGGTCGAGGACGGA-3': SEQ ID NO:14) were designed based on the AN12 crtO sequence and were used to amplify 1151 bp crtO internal fragment from ATCC 47072 with 275 bp truncation at the N-terminal and 173 bp truncation at the C-terminal end. The identity of the crtO amplified from ATCC 47072 was confirmed by sequencing and showed 95% identity at the DNA level to the *Rhodococcus* AN12 crtO. The crtO fragment was first cloned into pCR2.1 TOPO vector (Invitrogen, Carlsbad, Calif.). The TOPO clones were then digested with NcoI (NcoI restriction sites underlined in the primer sequences) and the internal crtO fragment from the TOPO clones was subsequently cloned into the NcoI site of pBR328. The resulting construct was confirmed by sequencing and designated pDCQ102. Approximately 1 µg DNA of pDCQ102 was introduced into *Rhodococcus* ATCC47072 by electroporation and plated on NBYE plates with 10 µg/ml tetracycline. The pBR328 vector does not replicate in *Rhodococcus*. The tetracycline resistant transformants obtained after 3–4 days of incubation at 30° C. were generated by chromosomal integration. Integration into the targeted crtO gene on the chromosome of ATCC 47072 was confirmed by PCR. The vector specific primers PBR3 (5'-AGCGGCATCAGCACCTTG-3': SEQ ID NO:15) and PBR5 (5'-GCCMTATGGACMCTTCTTC-3': SEQ ID NO:16), paired with the gene specific primers (outside of the insert on pDCQ102) I2_OP5 (5'-ACCTGAGGTGTTC-GACGAGGACMCCGA-3': SEQ ID NO:17) and I2_OP3 (5'-GTTGCACAGTGGTCATCGTGCCAGCCGT-3': SEQ ID NO: 18) were used for PCR using chromosomal DNA prepared from the tetracycline resistant transformants as the templates. PCR fragments of the expected size were amplified from the tetracycline resistant transformants, but no PCR product was obtained from the wild type ATCC 47072. When the two gene specific primers were used, no PCR fragment was obtained with the tetracycline resistant transformants due to the insertion of the large vector DNA. The PCR fragment obtained with the vector specific primers and the gene specific primers was sequenced. Sequence analysis of the junction of the vector and the crtO gene confirmed that a single crossover recombination event occurred at the expected site and disrupted the targeted crtO gene.

Colonies of the CrtO mutant were yellow as compared to the pink color seen in the wild type strain, suggesting that different carotenoid pigments were produced in the CrtO mutant. To extract the carotenoids from the CrtO mutant strain, 100 ml of cell culture in NBYE (0.8% nutrient broth +0.5% yeast extract) was grown at 26° C. overnight with shaking to the stationary phase. Cells were spun down at 4000 g for 15 min, and the cell pellets were resuspended in 10 ml acetone. Carotenoids were extracted into acetone with constant shaking at room temperature for 1 hour. The cells were spun down and the supernatant was collected. The extraction was repeated once, and the supernatants of both extractions were combined and dried under nitrogen. The dried material was re-dissolved in 0.5 ml methanol and insoluble material was removed by centrifugation at 16,000 g for 2 min in an Eppendorf microcentrifuge 5415C. 0.2 ml of the sample was used for HPLC analysis. A Beckman System Gold® HPLC with Beckman Gold Nouveau Software (Columbia, Md.) was used for the study. 0.1 ml of the crude acetone extraction was loaded onto a 125×4 mm RP8 (5 µm particles) column with corresponding guard column (Hewlett-Packard, San Fernando, Calif.). The flow rate was 1 ml/min and the Solvent program was 0–11.5 min linear gradient from 40% water/60% methanol to 100% methanol, 11.5–20 min 100% methanol, 20–30 min 40% water/60% methanol. Spectral data was collected using a Beckman photodiode array detector (model 168).

HPLC analysis showed that the CrtO mutant lacked the major carotenoid peak of the wild type strain. The major peak observed in the CrtO mutant was at an elution time of 15.6 min with an absorption maxima of 435 nm, 458 nm and 486 nm, which is identical to the characteristics of the minor peak of the wild type strain (FIG. 4). These results confirmed that CrtO mutant produced different carotenoids compared to the wild type strain.

Example 5

Evidence for Ketocarotenoid from Wild Type *Rhodococcus* ATCC 47072

Example 5 offers biochemical evidence for the production of ketocarotenoids from monocyclic and bicyclic carotenoids.

Some tests for particular functional groups on carotenoids may be conveniently carried out in a spectrophotometer cuvette and monitored for diagnostic changes in the spectrum. For example, reduction with $NaBH_4$ maybe used to diagnose the presence of aldehyde or ketone groups in a carotenoid. Reduction of a conjugated carbonyl group to the corresponding alcohol results in a hypsochromic shift (to shorter wavelengths) and increase in fine structure of the spectrum of the peak.

The round-shaped absorption (465 nm) of the wild type *Rhodococcus* major carotenoid indicated the presence of conjugated carbonyl function. Based on this finding a chemical reduction was performed by addition of 1 mg of $NaBH_4$ to 10 µg of the carotenoids produced from wild type ATCC 47072. The color of the carotenoids changed from pink to yellow in 2 min, which further suggested the presence of the ketone group in the carotenoids. The yellow reduction product was analyzed by HPLC and showed that the spectra of the major peak hypsochromically shifted from the round-shaped 465 nm (% III/II is zero) to the fine structure (435 nm, 458 nm, 486 nm, % III/II is 0.42) identical to the spectra of the minor peak of the wild type strain. However it eluted at 14.4 min, which was earlier than the minor peak of the wild type strain (15.6 min), suggesting that the reduction compound was more polar than the minor peak compound in the wild type strain. This is consistent with the presence of the ketone group in the major carotenoid of wild type strain, which was reduced to hydroxy group upon $NaBH_4$ reduction. The reduction compound with the hydroxy group was more polar than the wild type minor compound likely without the ketone or hydroxy group.

TABLE 1

Comparison of the pigments of wild type *Rhodococcus* ATCC47072 with and without NaBH4 reduction, and that of *Rhodococcus* CrtO mutant

| Strain | Colony color | Absorption spectra | % III/II[a] | Retention time |
|---|---|---|---|---|
| Wild type | Pink | Major (465 nm) | 0 | 14.6 min |
|  |  | Minor (435 nm, 458 nm, 486 nm) | 0.45 | 15.6 min |
| Wt/NaBH$_4$ | Yellow | Major (435 nm, 458 nm, 486 nm) | 0.42 | 14.4 min |
|  |  | Minor (435 nm, 458 nm, 486 nm) | 0.45 | 15.6 min |
| CrtO mutant | Yellow | Major (435 nm, 458 nm, 486 nm) | 0.45 | 15.6 min |

%III/II[a]. The peak height of the longest wavelength absorption band is designated as III, that of the middle absorption band as II. The base-line is taken as the minimum between the two peaks.
%III/II describes the fine structure of the spectrum.

Example 6

Determination of the Molecular Weight of the Major Carotenoid in *Rhodococcus* CrtO Mutant The major carotenoid in the *Rhodococcus* CrtO mutant was purified and the molecular weight was determined. The CrtO mutant was grown in 100 ml in NBYE (0.8% nutrient broth +0.5% yeast extract) at 26° C. overnight with shaking to the stationary phase. Cells were spun down at 4000 g for 15 min. Carotenoids were extracted from the cell pellet into methanol and saponified with 5% KOH in methanol overnight at room temperature. After saponification, the majority of carotenoids were extracted into hexane. The extracted sample was first passed through a silica gel column to separate from neutral lipids. The column (1.5 cm×20 cm) was packed with silica gel 60 (particle size 0.040–0.063 mm, EM Science, Gibbstown, N.J.) and washed with hexane. The carotenoids sample was loaded, washed with 95% hexane +5% acetone and eluted with 80% hexane +20% acetone. The eluted carotenoids were further separated on a reverse phase C18 thin layer chromatography (TLC) plate (J. T. Baker, Phillipsburg, N.J.) with 80% acetonitrile +20% acetone as the mobile phase. The major carotenoid band (Rf 0.5) was excised and eluted with acetone. The molecular weight (MW) of the purified carotenoid of ATCC 47072 CrtO mutant was determined by MALDI-MS to be 536 Dalton (559 Dalton for the sodiated form). This was also confirmed by LC-MS with APCI (atmospheric pressure chemical ionization) that showed the MW of the protonated compound to be 537 Dalton. The molecular weight of the major and minor carotenoid in the wild type ATCC 47072 was previously determined to be 550 Dalton and 536 Dalton, respectively (Provisional U.S. Application No. 60/285,910, incorporated herein by reference). The fine structure of the spectra analysis suggested that the major carotenoid of 550 Dalton has conjugated ketone group(s), and the minor carotenoid of 536 Dalton lacks the conjugated ketone group(s). The difference of the 14 Dalton is likely due to one ketone group addition in the major carotenoid ($CH_2$ to CO, addition of O and removal of 2H). The carotenoid in the CrtO mutant might have the same structure as the minor carotenoid in the wild type strain as suggested by the match of the molecular weight, the HPLC separation and spectra data (Example 4). CrtO possibly encodes a carotenoid ketolase that introducing ketone groups to produce keto-carotenoids. The ketone group addition was blocked in the CrtO mutant.

Example 7

Synthesis of Ketocarotenoids in *E. coli* by Heterologous Expression of *Rhodococcus* CrtO An *E. coli* MG1655 strain producing β-carotene was used as the expression host for the *Rhodococcus* crtO gene. This *E. coli* strain was constructed by cloning the crtEXYIB cluster from *P. stewartii*. The crtEXYIB cluster was amplified from *Pantoea stewartii* (ATCC 8199) by the following method. Primers were designed using the sequence from *Erwinia uredovora* to amplify a fragment by PCR containing the crt genes. These sequences included:

5'-ATGACGGTCTGCGCAAAAAAACACG-3'  (SEQ ID NO:44)

5'-GAGAAATTATGTTGTGGATTTGGAATGC-3'  (SEQ ID NO:45)

Chromosomal DNA was purified from *Pantoea stewartii* (ATCC no. 8199) and Pfu Turbo polymerase (Stratagene, La Jolla, Calif.) was used in a PCR amplifcation reaction under the following conditions: 94° C., 5 min; 94° C. (1 min)–60° C. (1 min)–72° C. (10 min) for 25 cycles, and 72° C. for 10 min. A single product of 6.3 kb was observed following gel electrophoresis. Taq polymerase (Perkin Elmer) was used in a ten minute 72° C. reaction to add additional 3' adenosine nucleotides to the fragment for TOPO cloning into pCR4-TOPO (Invitrogen, Carlsbad, Calif.). Following transformation to *E. coli* DH5α (Life Technologies, Rockville, Md.) by electroproation, several colonies appeared to be bright yellow in color indicating that they were producing a carotenoid compound. The 6.3 kb EcoRI fragment containing the crt gene cluster (crtEXYIB) was cloned into broad-host range vector pBHR1 (MoBiTec, LLC, Marco Island, Fla.) to form pBHR-crt1. The *E. coli* strain with pBHR-crt1 containing the wild type crtEXYIB gene cluster produced β-carotene. The chloramphenicol resistance gene promoter on pBHR1 vector likely directed the functional expression of the crt genes. The *Rhodococcus* crtO gene was amplified from *R. erythropolis* AN12 using primer: I2-N: ATGAGCGCATTTCTCGACGCC (SEQ ID NO.46) and I2-C: TCACGACCTGCTCGMCGAC (SEQ ID NO.47). The amplified 1.6 kb PCR product was cloned into pTrcHis2-TOPO expression vector. Two clones (pDCQ117 #3 and #9) of the correct orientation were transformed into the *E. coli* strain MG1655(pBHR-crt1) which synthesized β-carotene. The *E. coli* colonies which synthesized β-carotene were yellow. The *E. coli* MG1655(pBHR-crt1) transformed with pDCQ117 turned orange, indicating that β-carotene in the host strain had been converted to a new carotenoid(s).

Pigment from both transformants were analyzed by HPLC using the method as described in Example 4 and exhibited the same profile as in FIG. 5. The major peak comprising 92% of the pigments eluted at 13.8 min and had a round-shaped spectrum of λmax=475 nm. This is identical to the authentic standard of canthaxanthin purchased from Sigma. A minor peak comprising 6% of the pigments eluted at. 14.8 min and had a round-shaped spectrum of λmax=465 nm. This is similar to what has been reported for echinenone, an intermediate with only one keto group addition. Synthesis of the ketocarotenoids in *E. coli* demonstrated that *Rhodococcus* crtO encoded a carotenoid ketolase that is functional in *E. coli*.

Example 8

In Vitro Assay for Ketolase Activity of *Rhodococcus* CrtO

To further confirm if crtO encoded a ketolase, we assayed cell extracts of *E. coli* containing pDCQ117 for the presence of ketolase activity in vitro. The in vitro enzyme assay was performed using crude cell extract from *E. coli* TOP10 (pDCQ117) cells expressing crtO. 100 ml of LB medium containing 100 μg/ml ampicillin was inoculated with 1 ml fresh overnight culture of TOP10 (pDCQ117) cells. Cells were grown at 37° C. with shaking at 300 rpm until $OD_{600}$ reached 0.6. Cells were then induced with 0.1 mM IPTG and continued growing for additional 3 hrs. Cell pellets harvested from 50 ml culture by centrifugation (4000 g, 15 min) were frozen and thawed once, and resuspended in 2 ml ice cold 50 mM Tris-HCl (pH7.5) containing 0.25% TritonX-100. 10 μg of β-carotene substrate (Spectrum Laboratory Products, Inc.) in 50 μl of acetone was added to the suspension and mixed by pipetting. The mixture was divided into two tubes and 250 mg of zirconia/silica beads (0.1 mm, BioSpec Products, Inc, Bartlesville, Okla.) was added to each tube. Cells were broken by bead beating for 2 min, and cell debris was removed by spinning at 10000 rpm for 2 min in an Eppendorf microcentrifuge 5414C. The combined supernatant (2 ml) was diluted with 3 ml of 50 mM Tris pH 7.5 buffer in a 50 ml flask, and the reaction mixture was incubated at 30° C. with shaking at 150 rpm for different lengths of time. The reaction was stopped by addition of 5 ml methanol and extraction with 5 ml diethyl ether. 500 mg of NaCl was added to separate the two phases for extraction. Carotenoids in the upper diethyl ether phase was collected and dried under nitrogen. The carotenoids were re-dissolved in 0.5 ml of methanol, and 0.1 ml was used for HPLC analysis as described in Example 4.

HPLC analysis of the 2 hr and 16 hr reactions is shown in FIG. 6. Three peaks were identified at 470 nm in the 16 hr reaction mixture. When compared to standards, it was determined that the peak with a retention time of 15.8 min was β-carotene and the peak with retention time of 13.8 min was canthaxanthin. The peak at 14.8 min was most likely echinenone, the intermediate with only one ketone group addition. In the 2 hr reaction mixture, the echinenone intermediate was the only reaction product and no canthaxanthin was produced. Longer incubation times resulted in higher levels of echinenone and the appearance of a peak corresponding to canthaxanthin. Canthaxanthin is the final product in this step representing the addition of two ketone groups (Table 2). To confirm that the ketolase activity was specific for crtO gene, the assay was also performed with extracts of control cells that would not use β-carotene as the substrate. No product peaks were detected in the control reaction mixture.

In summary, the in vitro assay data confirmed that crtO encodes a ketolase, which converted β-carotene into canthaxanthin (two ketone groups) via echinenone (one ketone group) as the intermediate. This symmetric ketolase activity of *Rhodococcus* CrtO is different from what was reported for the asymmetric function of *Synechocystis* CrtO. We also examined the effect of the exogenous cofactors. Addition of 0.2–2 mM of NADPH, NADH or FAD to the reaction mixture did not stimulate the ketolase reaction, presumably the cofactor(s) needed for the reaction was saturated in the crude cell extract used for the assay.

TABLE 2

HPLC analysis of the in vitro reaction mixtures with *Rhodococcus* CrtO.

|  | Canthaxanthin 474 nm 13.8 min | Echinenone 459 nm 14.8 min | β-carotene 449 nm 474 nm 15.8 min |
|---|---|---|---|
| 0 hr | 0% | 0% | 100% |
| 2 hr | 0% | 14% | 86% |
| 16 hr | 16% | 28% | 56% |
| 20 hr | 30% | 35% | 35% |

Example 9

*Deinococcus* Gene DR0093 Encodes a CrtO-type of Ketolase

Although *Deinococcus* Gene DR0093 is currently annotated as a probable phytoene dehydrogenase in the database, it shares closes homology with the *Rhodococcus* crtO gene. The function of DR0093 was determined to see if it encodes a carotenoid ketolase or a phytoene dehydrogenase.

The DR0093 gene was expressed in *E. coli* essentially as described in Example 7. DR0093 was PCR amplified from the genomic DNA of *Deinococcus radiodurans* strain R1 (ATCC 13939) using primers crtI2_F (Deino) (5'-ATGCCGGATTACGACCTGATCG-3': SEQ ID NO:21) and crtI2_R (Deino) (5'-TCATTTCCAGCGCCTCCGCGTC-3': SEQ ID NO:22). The PCR product was cloned into pTrcHis2-TOPO expression vector (Invitrogen, Carlsbad Calif.), resulting in plasmid pDCQ126 with the *Deinococcus* crtO gene cloned in the forward orientation respective to the trc promoter on the vector. Expression of pDCQ126 in *E. coli* synthesizing β-carotene also produced ketocarotenoids (canthaxanthin and echinenone), which were characaterized as described in Example 7.

The in vitro enzyme assay was performed using crude cell extract of *E. coli* TOP10 (pDCQ126) incubated with β-carotene substrate. The assay procedure and the subsequent HPLC analysis was the same as described in Example 8. The results are summarized in Table 3. The in vitro activity assay confirmed that *Deinococcus* gene DR0093 encodes a CrtO-type of ketolase that similar to *Rhodococcus* CrtO, which can add two ketone groups to β-carotene to form canthaxanthin via echinenone.

TABLE 3

HPLC analysis of the in vitro reaction mixtures with *Deinococcus* CrtO.

|  | Canthaxanthin 474 nm 13.8 min | Echinenone 459 nm 14.8 min | β-carotene 449 nm 474 nm 15.8 min |
|---|---|---|---|
| 0 hr | 0% | 0% | 100% |
| 2 hr | 0% | 2% | 98% |
| 20 hr | 8% | 30% | 62% |

What is claimed is:

1. A method for the production of cyclic ketocarotenoid compounds comprising:
   (a) providing a host cell which produces monocyclic or bicyclic carotenoids;
   (b) transforming the host cell of (a) with an isolated nucleic molecule encoding the carotenoid ketolase enzyme as set forth in SEQ ID NO:4 ; and
   (c) growing the transformed host cell of (b) under conditions whereby a cyclic ketocarotenoid is produced.

2. A method according to claim 1 wherein the cyclic ketocarotenoid compounds are selected from a group consisting of canthaxanthin, astaxanthin, adonixanthin, adonirubin, echinenone, 3-hydroxyechinenone, 3'-hydroxyechinenone, 4-keto-gamma-carotene, 4-keto-rubixanthin, 4-keto-torulene, 3-hydroxy-4-keto-torulene, deoxyflexixanthin, and myxobactone.

3. A method according to claim 2 wherein the monocyclic or bicyclic carotenoids are selected from the group consisting of β-Carotene, γ-carotene, zeaxanthin, rubixanthin, echinenone and torulene.

4. A method according to claim 1 wherein the transformed host cell is selected from the group consisting of bacteria, yeast, filamentous fungi, algae, and green plants.

5. A method according to claim 4 wherein the transformed host cell is selected form the group of *Aspergillus, Trichoderma, Saccharomyces, Pichia, Candida, Hansenula*, or *Salmonella, Bacillus, Acinetobacter, Zymomonas, Agrobacterium, Erythrobacter Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas,Sphigomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*.

6. A method according to claim 4 wherein the transformed host cell is selected from the group consisting of *Spirulina, Haemotacoccus*, and *Dunalliela*.

7. A method according to claim 4 wherein the transformed host cell is selected from the group consisting of soybean, rapeseed, sunflower, cotton, corn, tobacco, alfalfa, wheat, barley, oats, sorghum, rice, *Arabidopsis*, cruciferous vegetables, melons, carrots, celery, parsley, tomatoes, potatoes, strawberries, peanuts, grapes, grass seed crops, sugar beets, sugar cane, beans, peas, rye, flax, hardwood trees, softwood trees, and forage grasses.

8. A method of regulating cyclic ketocarotenoid biosynthesis in an organism comprising,
   (a) introducing into a host cell an isolated nucleic acid molecule encoding the carotenoid ketolase as set forth in SEQ ID NO:4 said isolated nucleic acid molecule under the control of suitable regulatory sequences; and
   (b) growing the host cell of (a) under conditions whereby the nucleic acid encoding the carotenoid ketolase is expressed and cyclic ketocarotenoid biosynthesis is regulated.

9. A method according to claim 8 wherein the nucleic acid encoding the carotenoid ketolase is upregulated.

10. A method according to claim 9 wherein said nucleic acid encoding the carotenoid ketolase is over-expressed on a multicopy plasmid.

11. A method according to claim 9 wherein said nucleic acid encoding the carotenoid ketolase is operably linked to an inducible or regulated promoter.

12. A method according to claim 8 wherein the nucleic acid encoding the carotenoid ketolase is down-regulated.

13. A method according to claim 12 wherein said nucleic acid encoding the carotenoid ketolase is expressed in antisense orientation.

14. A method according to claim 12 wherein said nucleic acid encoding the carotenoid ketolase is disrupted by insertion of foreign DNA into the coding region.

* * * * *